(12) United States Patent
Doyle et al.

(10) Patent No.: US 8,163,944 B2
(45) Date of Patent: Apr. 24, 2012

(54) ALLYLIC OXIDATIONS CATALYZED BY DIRHODIUM CATALYSTS UNDER AQUEOUS CONDITIONS

(75) Inventors: Michael P. Doyle, Glenn Dale, MD (US); Arthur J. Catino, College Park, MD (US); Hojae Choi, Ellicott City, MD (US); Jason M. Nichols, Silver Spring, MD (US)

(73) Assignee: University of Maryland College Park, College Park, MD (US)

( * ) Notice: Subject to any disclaimer, the term of this patent is extended or adjusted under 35 U.S.C. 154(b) by 346 days.

(21) Appl. No.: 12/246,324

(22) Filed: Oct. 6, 2008

(65) Prior Publication Data

US 2009/0093638 A1 Apr. 9, 2009

Related U.S. Application Data

(60) Provisional application No. 60/978,206, filed on Oct. 8, 2007.

(51) Int. Cl.
*C07C 59/00* (2006.01)
*C07C 45/00* (2006.01)
*C07J 13/00* (2006.01)
*C07J 9/00* (2006.01)

(52) U.S. Cl. ........ 552/544; 552/534; 552/540; 562/577; 568/342; 568/385

(58) Field of Classification Search ........... 562/100, 562/577; 552/534, 540, 544; 568/342, 385
See application file for complete search history.

(56) References Cited

U.S. PATENT DOCUMENTS

| | | | |
|---|---|---|---|
| 4,309,310 | A | 1/1982 | Callahan et al. |
| 6,274,746 | B1 | 8/2001 | Marwah et al. |
| 6,384,251 | B1 | 5/2002 | Marwah et al. |
| 6,686,486 | B1 | 2/2004 | Marwah et al. |
| 2006/0211870 | A1 | 9/2006 | Doyle |
| 2009/0093638 | A1 | 4/2009 | Doyle et al. |

FOREIGN PATENT DOCUMENTS

WO WO98/50409 11/1998

OTHER PUBLICATIONS

Chavez, F.A. et al. (2000) "Co(III)-Alkylperoxo Complexes: Syntheses, Structure-Reactivity Correlations, and Use in the Oxidation of Hydrocarbons," Acc. Chem. Res. 33:539-545.
Chen, M.S. et al. (2004) "A Sulfoxide-Promoted, Catalytic Method for the Regioselective Synthesis of Allylic Acetates from Monosubstituted Olefins via C-H Oxidation," J. Am. Chem. Soc. 126:1346-1347.

(Continued)

*Primary Examiner* — Taylor Victor Oh
(74) *Attorney, Agent, or Firm* — William C. Schrot; Jeffrey I. Auerbach; The Auerbach Law Firm, LLC

(57) ABSTRACT

The present invention relates to compositions and methods for achieving the efficient allylic oxidation of organic molecules, especially olefins and steroids, under aqueous conditions. The invention concerns the use of dirhodium (II,II) "paddlewheel complexes, and in particular, dirhodium carboximate and tert-butyl hydroperoxide as catalysts for the reaction. The use of aqueous conditions is particularly advantageous in the allylic oxidation of 7-keto steroids, which could not be effectively oxidized using anhydrous methods, and in extending allylic oxidation to enamides and enol ethers.

16 Claims, 4 Drawing Sheets

OTHER PUBLICATIONS

Chifotides, H.T. et al. (2005) *"Interactions of Metal-Metal-Bonded Antitumor Active Complexes with DNA Fragments and DNA,"* Acc. Chem. Res. 38:146-156.

Chiu, P. et al. (2004) *"An Expeditious Nazarov Cyclization Strategy toward the Hydroazulene Core of Guanacastepene A,"* Org. Lett 6:613-616.

Choi, H. et al. (2007) *"Optimal TBHP Allylic Oxidation of $\Delta^5$-Steroids Catalyzed by Dirhodium Caprolactamate,"* Org. Lett. 9:5349-5352.

Crich, D. et al. (2004) *"Catalytic Allylic Oxidation with a Recyclable, Fluorous Seleninic Acid,"* Org. Lett. 6:775-777.

Dang, H. et al. (1990) *"Reactivities of Some Hydroperoxides Toward Allylic Rearrangement and Related Reactions,"* J. Org. Chem. 55:1432-1438.

Davis, R.A. (2005) *"Isolation and Structure Elucidation of the New Fungal Metabolite (−)-Xylariamide A,"* J. Nat. Prod. 68:769-772.

Delcamp, J.H. et al. (2006) *"Sequential Hydrocarbon Functionalization: Allylic C-H Oxidation/Vinylic C-H Arylation,"* J. Am. Chem. Soc. 128:15076-15077.

Doyle, M. P. et al. (2001) *"The Influence of Ligands on Dirhodium(II) on Reactivity and Selectivity in Metal Carbene Reactions,"* Prog. Inorg. Chem. 49:113-168.

Doyle, M.P. (1995) *"Enantiomer Differentiation in Intramolecular Carbon-Hydrogen Insertion Reactions of Racemic Secondary Alkyl Diazoacetates Catalyzed by Chiral Dirhodium(II) Carboxamidates,"* Russ. Chem. Bull. 44:1729-1734.

Doyle, M.P. et al. (1993) *"Dirhodium(II) Tetrakis(Carboxamidates) with Chiral Ligands. Structure and Selectivity in Catalytic Metal Carbene Transformations,"* J. Am. Chem. Soc. 115:9968-9978.

Doyle, M.P. et al. (1993) *"Electronic and Steric Control in Carbon-Hydrogen Insertion Reactions of Diazoacetoacetates Catalyzed by Dirhodium(II) Carboxylates and Carboxamides,"* J. Am. Chem. Soc. 115:958-964.

Doyle, M.P. et al. (1995) *"Enhancement of Enantiocontrol/Diastereocontrol in Catalytic Intramolecular Cyclopropanation and Carbon-Hydrogen Insertion Reactions of Diazoacetates with Rh2(4S-MPPIM)4"* Tetrahedron Lett. 36:7579-7582.

Doyle, M.P. et al. (1995) *"Highly Enantioselective Route to β-Lactams via Intramolecular C-H Insertion Reactions of Diazoacetylazacyclo-alkanes Catalyzed by Chiral Dirhodium(II) Carboxamidates,"* Synlett 1075-1076.

Doyle, M.P. et al. (1995) *"Optimization of Enantiocontrol for Carbon-Hydrogen Insertion with Chiral Dirhodium(II) Carboxamidates. Synthesis of Natural Dibenzylbutyrolactone Lignans from 3-Aryl-1-propyl Diazoacetates in High Optical Purity,"* J. Org. Chem. 60:6654-6655.

Doyle, M.P. et al. (1996) *"Chiral Dirhodium Carboxamidates. Catalysts for Highly Enantioselective Syntheses of Lactones and Lactams,"* Aldrichimica Acta 29(1):3-11.

Doyle, M.P. et al. (1996) *"Highly Enantioselective Intramolecular Cyclopropanation Reactions of N-Allylic-N-methyldiazoacetamides Catalyzed by Chiral Dirhodium(II) Carboxamidates,"* J. Org. Chem. 61:2179-2184 (1996).

Doyle, M.P. et al. (1997) *"Highly Enantioselective Oxonium Ylide Formation and Stevens Rearrangement Catalyzed by Chiral Dirhodium(II) Carboxamidates,"* Tetrahedron Lett. 38:4367-4370.

Ahsan, M.Q. et al. (1986) *"Reaction of Tetrakis(Acetato)Dirhodium With Acetamide: Crystal and Molecular Structure of Tetrakis(Acetamido)Diaquadirhodium Trihydrate,"* Inorg. Chem. 25:260.

Arigoni, D. et al. (1973) *"Selenium Dioxide Oxidations of Olefins. Trappings of the Allylic Seleninic Acid Intermediate as a Seleninolactone,"* J. Am. Chem. Soc. 95(23):7917-7919.

Arsenou, E.S. et al. (2003) *"Optimization of the Allylic Oxidation in the Synthesis of 7-Keto-±D5-Steroidal Substrates,"*Steroids 68:407-414.

Avila, D.V. et al. *"Dramatic Solvent Effects on the Absolute Rate Constants for Abstraction of the Hydroxylic Hydrogen Atom from tert-Butyl Hydroperoxide and Phenol by the Cumyloxyl Radical. The Role of Hydrogen Bonding,"* (1995) J. Am. Chem. Soc. 117:2929-2930.

Ballini, R. et al. (1996) *"Convenient Synthesis of (E)-Non-3-ene-2,5-dione, an Important Component Isolated from the Fire Bee Trigona tataira"* Liebigs Ann.11:1879-1880.

Ballini, R. et al. (1998) *"Synthesis of (E)-4-Oxonon-2-enoic Acid, a Natural Antibiotic Produced by Streptomyces olivaceus,"* J. Nat. Prod. 61:673-674.

Beckwith, A.L.J. et al. (1989) *"The Mechanisms of the Rearrangements of Allylic Hydroperoxides: 5-Hydroperoxy-3-Hydroxycholest-6-Ene and 7-Hydroperoxy-3-Hydroxycholest-5-Ene,"* J. Chem. Soc. Perkin Trans. 2:815-824.

Bhalerao, U.T. et al. (1971) *"Stereochemistry of Allylic Oxidation with Selenium Dioxide. Stereospecific Oxidation of gem-Dimethyl Olefins,"* J. Am. Chem. Soc. 93(19):4835-4840.

Blanksby, S.J. et al. (2003) *"Bond Dissociation Energies of Organic Molecules,"* Acc. Chem. Res. 36:255-263.

Blay, G. et al. (2001) *"Alkane Oxidation by a Carboxylate-Bridged Dimanganese(III) Complex,"* Chem. Comm. 11:2102-2104.

Bode, J.W. et al. (1996) *"Intramolecular Regioselective Insertion into Unactivated Prochiral Carbon-Hydrogen Bonds with Diazoacetates Catalyzed by Chiral Dirhodium(II) Carboxamidates. Highly Enantioselective Total Synthesis of Natural Lignan Lactones,"* J. Org. Chem. 61:9146-9155.

Bravo, A. et al. (1997) *"Ingold-Fischer "Persistent Radical Effect", Solvent Effect, and Metal Salt Oxidation of Carbon-Centered Radicals in the Synthesis of Mixed Peroxides from tert-Butyl Hydroperoxide,"* J. Org. Chem. 62:3849-3857.

Catino, A.J. et al. (2004) *"Dirhodium(II) Caprolactamate: An Exceptional Catalyst for Allylic Oxidation,"* J. Am. Chem. Soc. 126:13622-13623.

Catino, A.J. et al. (2005) *"Efficient Aziridination of Olefins Catalyzed by Mixed-Valent Dirhodium(II,III) Caprolactamate,"* Org. Lett. 7:2787.

Catino, A.J. et al. (2005) *"Benzylic Oxidation Catalyzed by Dirhodium(II,III) Caprolactamate,"* Org. Lett., 7(23):5167-5170.

Catino, A.J. et al. (2006) *"The Oxidative Mannich Reaction Catalyzed by Dirhodium Caprolactamate,"* J. Amer. Chem. Soc. 128:5648-5649.

Caudle, M.T. et al. (1996) *"Mechanism for the Homolytic Cleavage of Alkyl Hydroperoxides by the Manganese(III) Dimer $Mn^{III}{}_2$(2-OHsalpn)$_2$,"* Inorg. Chem. 35:3577-3584.

Chavan, M.Y. et al. (1984) *"Axial-Ligand-Dependent Electrochemical and Spectral Properties of a Series of Acetate- and Acetamidate-Bridged Dirhodium Complexes,"* Inorg. Chem. 23:4538.

ALLYLIC OXIDATIONS CATALYZED BY DIRHODIUM CATALYSTS UNDER AQUEOUS CONDITIONS

CROSS-REFERENCE TO RELATED APPLICATIONS

This application claims priority to U.S. Patent Application Ser. No. 60/978,206 (filed Oct. 8, 2007; pending), which application is herein incorporated by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of NSF CHE0456911 and NIH RO1GM046503 awarded by the National Science Foundation and the National Institutes of Health, respectively.

BACKGROUND OF THE INVENTION

1. Field of the Invention

The present invention relates to compositions and methods for achieving the efficient allylic oxidation of organic molecules, especially olefins and steroids, under aqueous conditions. The invention concerns the use of dirhodium (II,II) "paddlewheel complexes, and in particular, dirhodium carboximate as catalyst and tert-butyl hydroperoxide as oxidant for the reaction. The use of aqueous conditions is particularly advantageous in the allylic oxidation of delta-4 and delta-5 steroids, which could not be effectively oxidized using anhydrous methods, and in extending allylic oxidation to enamides and enol ethers.

2. Description of Related Art

Allylic oxidation holds a venerable position in organic synthesis. The regioselective functionalization of an allylic C—H bond with oxygen is a value-added operation yielding a wide range of synthetically useful products, including the direct synthesis of enones and enediones from the oxidation of readily available alkenes (Catino, A. J. et al. (2004) "*Dirhodium (II) Caprolactamate: An Exceptional Catalyst for Allylic Oxidation,*" J. Am. Chem. Soc. 126:13622-13623).

Non-catalytic methods for achieving allylic oxidation have been disclosed (e.g., methods employing stoichiometric chromic acid derivatives and selenium dioxide) (see e.g., U.S. Pat. No. 6,384,251; Arigoni, D. et al. (1973) J. Am. Chem. Soc. 95(23):7917-7919; Umbreit, M. A. et al. (197) "*Allylic Oxidation Of Olefins By Catalytic And Stoichiometric Selenium Dioxide With tert-Butyl Hydroperoxide,*" J. Am. Chem. Soc. 99:5526-5528; Rapoport, H. et al. (1971) J. Am. Chem. Soc. 93(19):4835-4840; Stephenson, L. M. et al. (1979) J. Org. Chem. 44(25):4683-4689; Pearson, A. J. et al. Tetrahedron Lett. (1984) 25:1235; Rabjohn, N. (1976) "*Selenium Dioxide Oxidation,*" Org. React. 24:261-415; Crich, D. et al. (2004) "*Catalytic Allylic Oxidation with a Recyclable, Fluorous Seleninic Acid,*" Org. Lett. 6:775-777; Zeni, G. et al. (2003) "*A Convenient Preparation Of Chalcogenoenynes From β-Bromovinyl Ketene Chalcogenoacetals,*" Synlett 12:1880-1882; Shing, T. M. K. et al. (2005) "*Total Synthesis Of (−)-Samaderine Y From (S)-(+)-Carvone,*" Angew. Chem. Int. Ed. 44:7981-7984; Hua, Z. et al. (2005) "*The Synthesis and Preliminary Biological Evaluation of a Novel Steroid with Neurotrophic Activity: NGA0187,*" J. Org. Chem. 70:9849-9856; Salmond, W. G. et al. (1978) "*Allylic Oxidation With 3,5-Dimethylpyrazole. Chromium Trioxide. Complex Steroidal .DELTA.5-7-Ketones,*" J. Org. Chem. 43:2057-2059).

However, the selective oxidative functionalization of allylic, benzylic and steroidal hydrocarbons using transition metal catalysis has been a long-standing goal in organic process development (Catino, A. J. et al. (2005) Org. Lett., 7(23): 5167-5170). Because of the stabilization offered to reaction intermediates, allylic and benzylic oxidations have been preferred targets, and peroxide-based oxidants (and in particular, tert-butyl hydroperoxide ("TBHP") have been the reagents of choice (Catino, A. J. et al. (2005) Org. Lett., 7(23):5167-5170; Bulman Page, P. C.; McCarthy, T. J. In COMPREHENSIVE ORGANIC SYNTHESIS; Trost, B. M., Ed.; Pergamon: Oxford, UK, 1991; Vol. 7, p 83; Olah, G. A.; Molnár, Á. Oxidation-Oxygenation. In HYDROCARBON CHEMISTRY, 2nd ed; Wiley: Hoboken; 2003; p 427.

In particular, such oxidative functionalizations have been achieved using TBHP in conjunction with the transition-metal catalyst, dirhodium(II,III) tetrakis(caprolactamate) ("$Rh_2(cap)_4$") (Catino, A. J. et al. (2005) Org. Lett. 7:2787; Catino, A. J. et al. (2006) J. Amer. Chem. Soc. 128:5648-5649; Catino, A. J. et al. (2004) "*Dirhodium(II) Caprolactamate: An Exceptional Catalyst for Allylic Oxidation,*" J. Am. Chem. Soc. 126:13622-13623; Catino, A. J. et al. (2005) Org. Lett., 7(23):5167-5170).

Reaction rates are slow (requiring multiple hours to come to completion), and yields have been found to be heavily dependent on the employed solvents, with the reaction yield increasing with decreasing solvent polarity (Miller, R. A. et al. (1996) "*A Ruthenium Catalyzed Oxidation Of Steroidal Alkenes To Enones,*" Tetrahedron Lett. 37:3429-3432). Suitable solvents have included 1,2 dichloroethane ("DCE") and dichloromethane (Catino, A. J. et al. (2005) Org. Lett., 7(23): 5167-5170). Inorganic base (and in particular, $(NH_4)_2CO_3$, $NaHCO_3$ or $(NH_4)OAc$ has been shown to enhance reaction yield (Catino, A. J. et al. (2005) Org. Lett., 7(23):5167-5170). Miller, R. A. et al. (1996) reported the use of an aqueous preparation of TBHP ("T-HYDRO®," 70% TBHP in water; Aldrich Chemical Company) and ruthenium trichloride to achieve the oxidation of steroidal alkenes to enones (Miller, R. A. et al. (1996) "*A Ruthenium Catalyzed Oxidation Of Steroidal Alkenes To Enones,*" Tetrahedron Lett. 37:3429-3432). Shultz et al. disclosed the use of pyridinium dichromate and TBHP to catalyze the oxidation of olefin (Schultz, A. G. et al. J. Org. Chem. (1998) 63:7795). This procedure has been applied to the oxidation of $\Delta^5$-steroids (Fousteris, M. A. et al. (2006) "*Improved Chromium-Catalyzed Allylic Oxidation Of Δ5-Steroids With T-Butyl Hydroperoxide,*" J. Mol. Catal. A: Chem. 250:70-74). Corey et al. described a catalytic allylic oxidation for the conversion of α,β-enones into 1,4-enediones using palladium-catalysis (Yu, J.-Q. et al. (2003) "*A Mild, Catalytic, and Highly Selective Method for the Oxidation of α,β-Enones to 1,4-Enediones,*" J. Am. Chem. Soc. 125:3232-3233; Yu, J.-Q. et al. (2002) "*Diverse Pathways for the Palladium(II)-Mediated Oxidation of Olefins by tert-Butylhydroperoxide,*" Org. Lett. 4:2727-2730; Yu, J.-Q. et al. (2005) "*Pd(OH)$_2$/C-Mediated Selective Oxidation of Silyl Enol Ethers by tert-Butylhydroperoxide, a Useful Method for the Conversion of Ketones to α,β-Enones or β-Silyloxy-α,β-enones,*" Org. Lett. 7:1415-1417).

Mechanistically, it was proposed that oxidation proceeds through an unusual $Pd^{2+}/Pd^{1+}$ catalytic cycle. Treatment of $Pd^{II}(OH)_2$ with TBHP generates $Pd^{II}(OO^tBu)_2$ which homolytically dissociates to form $Pd^{I}(OO^tBu)$ and tert-butyl peroxy radical. Hydrogen atom abstraction generates a carbon-centered radical.

Applications in natural product synthesis using palladium-catalyzed allylic oxidation have recently appeared due to the ease of using commercial Pd(OH)$_2$/C, mild reaction conditions, and selectivity. For example, a palladium-catalyzed allylic oxidation was used in the synthesis of the hydroazulene of guanacastepene A, a diterpenoid that exhibits potency against methicillin-resistant and vancomycin-resistant pathogens (Chiu, P. et al. Org. Lett (2004) 6:613). Using slightly modified conditions, hydroazulene has been oxidized in 65% yield over 48 hours at 40° C. (see, Magnus, P. et al. Org. Lett. (2005) 7:3853; Manzano, F. L. et al. Org. Lett. (2006) 8:2879). Recently, Shing, T. K. M. et al. described a metal-catalyzed allylic oxidation of a cyclic olefin (Shing, T. M. K. et al. (2005) "*Total Synthesis Of (−)-Samaderine Y From (S)-(+)-Carvone*," Angew. Chem. Int. Ed. 44:7981-7984). Shing and coworkers further reported the allylic oxidation of a wide range of substrates catalyzed by manganese(III) acetate (Mn(OAc)$_3$.2H$_2$O) in conjunction with anhydrous TBHP (Shing, T. K. M. et al. (2006) "*Mild Manganese(III) Acetate Catalyzed Allylic Oxidation: Application to Simple and Complex Alkenes*," Org. Lett. 8:3149-3151). The reaction was particularly amenable to allylic oxidation of $\Delta^5$-steroids to $\Delta^5$-en-7-ones. Molecular sieves were required to remove deleterious water that was shown to cause catalyst destruction. The manganese-catalyzed allylic oxidation was also extended to simple cyclic alkenes. The reactions were both chemo- and regio-selective across a broad range of substrates.

The oxidative MANNICH REACTION involves the direct catalytic C—H oxidation of a tertiary amine followed by nucleophilic capture. In light of the ability of Rh$_2$(cap)$_4$ to mediate allylic and benzylic oxidation in conjunction with TBHP, the ability of these reagents to mediate the MANNICH REACTION was assessed by Catino, A. J. et al. (2006) and found to be capable of mediating a MANNICH REACTION with N,N-dimethylaniline (Catino, A. J. et al. (2006) J. Amer. Chem. Soc. 128:5648-5649). Catino, A. J. et al. (2006) reported that since iminium ions (the MANNICH REACTION intermediate) were known to be stabilized by polar solvents, an aqueous preparation of TBHP ("T-HYDRO®," 70% TBHP in water) was employed. (Catino, A. J. et al. (2006) J. Amer. Chem. Soc. 128:5648-5649).

Despite all such advances, a need remains for improved methods of allylic oxidation, particularly methods capable of oxidizing alkenes at their allylic position to unsaturated carbonyl compounds (or arenes at their benzyllic position) when these reactions are catalyzed under aqueous conditions. Of particular importance are such methods that would be applicable to sterols, terpenes and unsaturated fatty acids, which are not oxidized by prior procedures that employ non-aqueous media. The present invention is directed to this and other goals.

SUMMARY OF THE INVENTION

Dirhodium(II) caprolactamate exhibits optimal efficiency for the production of the tert-butylperoxy radical, which is a selective reagent for hydrogen atom abstraction. These oxidation reactions occur with aqueous tert-butyl hydroperoxide (TBHP) without rapid hydrolysis of the caprolactamate ligands on dirhodium. Allylic oxidations of enones yield the corresponding enedione in moderate to high yields, and applications include allylic oxidations of steroidal enones. Although methylene oxidation to a ketone is more effective, methyl oxidation to a carboxylic acid can also be achieved. The invention reflects, in part, the recognition that dirhodium (II) caprolactamate exhibits superior efficiency as a catalyst for allylic oxidations, benzylic oxidations, aziridinations, and related reactions by TBHP (mol % catalyst, % conversion) under aqueous conditions.

The present invention thus relates to compositions and methods for achieving the efficient allylic oxidation of organic molecules, especially olefins and steroids, under aqueous conditions. The invention concerns the use of dirhodium (II,II) "paddlewheel complexes, and in particular, dirhodium carboxamidate and tert-butyl hydroperoxide as catalysts for the reaction. The use of aqueous conditions is particularly advantageous in the allylic oxidation of 7-keto steroids, which could not be effectively oxidized using anhydrous methods, and in extending allylic oxidation to enamides and enol ethers.

In detail, the invention provides a method for conducting oxidation of an allylic group of a compound, which comprises incubating a compound containing an allylic group in the presence of:
(A) a mixed-valent dirhodium(II,III) catalyst (Rh$_2^{5+}$); and
(B) an aqueous solution of tert-butyl hydroperoxide under conditions sufficient to oxidize the allylic group of the compound.

The invention further concerns the embodiment of such method, wherein the mixed-valent dirhodium(II,III) catalyst (Rh$_2^{5+}$) is an analogue or derivative of a member of the carboxamidate class of dirhodium(II,II) paddlewheel complexes, and in particular, wherein the arms of the carboxamidate class of dirhodium(II,II) paddlewheel complexes comprises seven membered rings. The invention particularly concerns the embodiment of such method wherein the mixed-valent dirhodium(II,III) catalyst (Rh$_2^{5+}$) is dirhodium(II,II) caprolactamate [Rh$_2$(cap)$_4$], or a derivative or analogue thereof.

The invention further concerns the embodiments of such methods, wherein the compound is dissolved in an organic solvent (and especially wherein the organic solvent is dichloroethane or dichloromethane).

The invention further concerns the embodiments of such methods, wherein the mixed-valent dirhodium(II,III) catalyst (Rh$_2^{5+}$) is present in the incubation at 0.4-0.6 molar equivalents.

The invention further concerns the embodiments of such methods, wherein the tert-butyl hydroperoxide is present in the incubation at 4-5 molar equivalents.

The invention further concerns the embodiments of such methods, wherein the compound comprises an optionally substituted $C_5$-$C_{12}$ alkenyl moiety that contains the allylic group, an optionally substituted cyclohexene moiety that contains the allylic group or is bonded to a carbon containing an allylic methylene group, or an optionally substituted aromatic moiety that contains the allylic group or is bonded to a carbon containing an allylic methylene group, or an optionally substituted steroidal moiety that contains the allylic group, wherein the steroidal moiety has the structure:

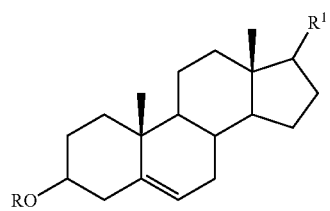

wherein R is H or an optionally substituted C2-C8 alkyl or alkenyl group and R1 is O or an optionally substituted C2-C8 alkyl or alkenyl group.

The invention further concerns the embodiments of such methods, wherein the compound has the structure:

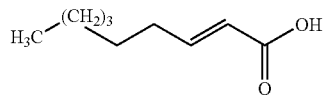

and the method results in the production of a compound having the structure:

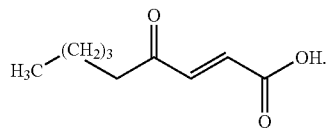

The invention further concerns the embodiments of such methods, wherein the compound comprises an enone moiety that contains the allylic group, or wherein the compound comprises an enamide moiety that contains the allylic group, or wherein the compound comprises an enol ether moiety that contains the allylic group.

DETAILED DESCRIPTION OF THE INVENTION

Figure 1:
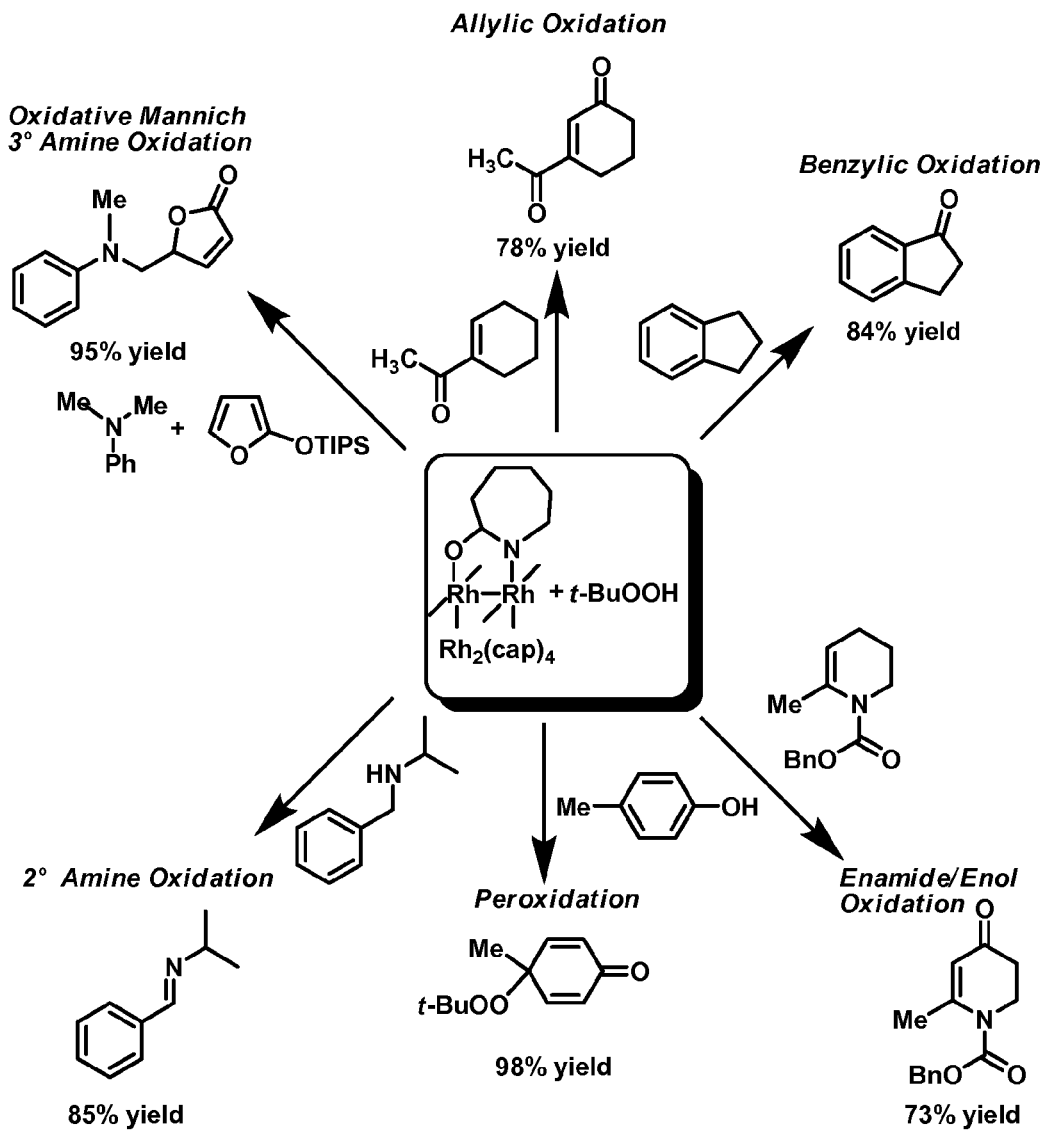
FIG. 1 illustrates the range of reactions catalyzed by dirhodium catalysts.

Stoichiometric metal oxidants have traditionally been employed to mediate the regioselective functionalization of an allylic C—H bond with oxygen. Although transition metal catalyzed processes comprise an improved method of mediating such functionalization, high catalyst loading, harsh anhydrous reaction conditions and poor selectivity have limited this advance. The present invention relates to compositions and methods for achieving the efficient allylic oxidation of organic molecules, especially olefins and steroids, under aqueous conditions. The invention concerns the use of dirhodium (II,II) "paddlewheel complexes, and in particular, dirhodium carboximate as catalyst and tert-butyl hydroperoxide as the oxidant for the reaction. The use of aqueous conditions is particularly advantageous in the allylic oxidation of 7-keto steroids, which could not be effectively oxidized using anhydrous methods, and in extending allylic oxidation to enamides and enol ethers.

Allylic oxidations (oxidations of an allylic methylene group) are of fundamental importance in synthetic organic chemistry, and a variety of reagents have been used for this transformation (Bulman-Page, P. C. et al. *In Comprehensive Organic Synthesis*; Trost, B. M., Ed.; Pergamon: Oxford, UK, 1991; Vol. 7.; Olah, G. A. et al. In *Hydrocarbon Chemistry*, 2nd ed.; Wiley: Hoboken; 2003). An allyl group is an alkene hydrocarbon group with the formula $R_2C=CR-CH_2-$, where R is either H or C—. It is composed of an alkenyl group ($R_2C=CR-$) bonded to a methylene group. The methylene group of such a compound is referred to as an allylic methylene group.

As used herein, the term "allylic oxidation" refers to the oxidation of an allylic methylene group to form either an allylic alcohol or a ketone. The allylic group being oxidized may be in a ring (especially a 6 membered ring) or it may be in an open chain structure.

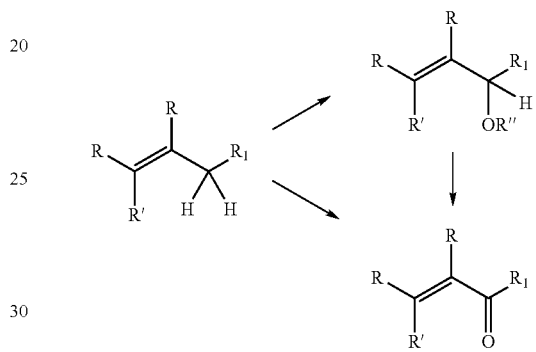

where R or R' is independently selected as H or C—, $R_1$ is C—, and R" is H or OR.

Allylic Oxidation

As used herein, the term "benzylic oxidation" refers to an allylic oxidation in which the alkenyl group (—CH=CH—) that is bonded to the allylic methylene group is a component of an aromatic ring or an aromatic ring system:

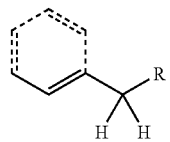

where R is H or C

The methods of the present invention may be employed to mediate the oxidation of allylic groups of diverse organic compounds. In particular, such methods may be used to mediate the oxidation of an allylic group of an optionally substituted $C_5$-$C_{12}$ alkenyl moiety, cyclohexene moiety, or steroidal moiety that contains the allylic group. As used herein, the term "optionally substituted" denotes that one or more of carbon atom(s) is/are independently and optionally substituted with N, S, O, or a halogen. As used herein, the term "$C_5$-$C_{12}$ alkenyl moiety" denotes a branched or unbranched chain of carbon atoms having one or more than one double bond. The term "cycloalkenyl moiety" denotes a non-aromatic ring structure (preferably composed of six members ("cyclohexenyl")) having one or more than one double bond. As used herein, the term "steroidal moiety" refers to a moiety having the structure:

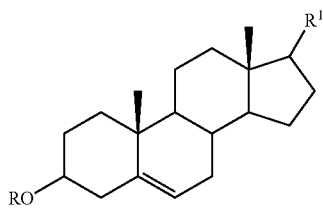

wherein R is H or an optionally substituted $C_2$-$C_8$ alkyl or alkenyl group and R1 is O or an optionally substituted $C_2$-$C_8$ alkyl or alkenyl group. The term "enone moiety" denotes a ketone moiety having an α,β-carbon-carbon double bond:

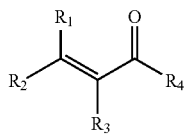

wherein $R^1$, $R^2$, $R^3$ and $R^4$ are independently alkyl, aryl or H and $R^2$ and $R^3$ or $R^3$ and $R^4$ may be linked together. As used herein, an enol ether is an alkene having an alkoxy group:

—CH=CH—O—R where R an alkyl or an aryl group. As used herein, the term "enamide moiety" refers to a moiety having the structure:

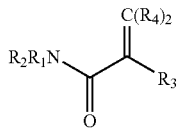

wherein $R^1$, $R^2$, and $R^3$ are independently alkyl, aryl or H, and $R^4$ is possesses an oxidizable $CH_2$ group.

Rhodium Catalysts

The present invention involves the use of a mild, selective, and efficient allylic oxidation protocol that involves aqueous catalysis mediated by a mixed-valent dirhodium(II,III) catalyst ($Rh_2^{5+}$):

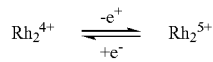

Rhodium compounds, and in particular, dirhodium (II,II) "paddlewheel" complexes can be made to undergo a transformation to form such mixed-valent catalysts. As used herein, a dirhodium (II,II) "paddlewheel" complex is a molecule having the general schematic structure (■), in which two rhodium ions are bonded together and their coordinate x,y,z axes are components of ring structures, so as to form a "paddlewheel-like" shape.

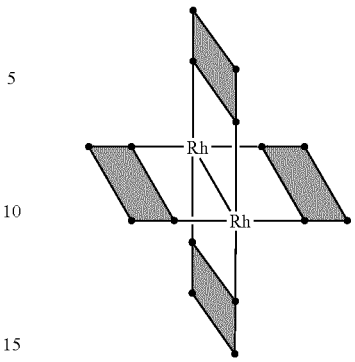

(I)

Exemplary dirhodium (II,II) "paddlewheel" complexes are disclosed by: Doyle, M. P. et al. (2001) "The Influence of Ligands on Dirhodium(II) on Reactivity and Selectivity in Metal Carbene Reactions," Prog. Inorg. Chem. 49:113-168, Ren, T. (1998) "Substituent Effects in Dinuclear Paddlewheel Compounds: Electrochemical and Spectroscopic Investigations," Coord. Chem. Rev. 175:43-58; D. Timmons and M. P. Doyle, "Chiral Dirhodium(II) Catalysts and their Applications," In METAL BONDS BETWEEN METAL ATOMS, Third Edition, F. A. Cotton, C. A. Murillo, and R. A. Walton, Eds., Springer Science and Business Media, New York, 2005, Chapter 13; Duncan, J. et al. (1982) "Characterization Of Novel Rhodium (II) Dimers With N-Phenylacetamido Bridging Ligands," J. Am. Chem. Soc. 104:5507; Chavan, M. Y. et al. (1984) "Axial-Ligand-Dependent Electrochemical And Spectral Properties Of A Series Of Acetate-And Acetamidate-Bridged Dirhodium Complexes," Inorg. Chem. 23:4538; Ahsan, M. Q. et al. (1986) "Reaction Of Tetrakis(Acetato)Dirhodium With Acetamide: Crystal And Molecular Structure Of Tetrakis(Acetamido)Diaquadirhodium Trihydrate," Inorg. Chem. 25:260; Lifsey, R. S. et al. (1987) "Reaction Of Rhodium(II) Acetate With N-Phenylacetamide: Substitution Products And Geometric Isomers," Inorg. Chem. 26: 830; M. P. Doyle, T. Ren, In Progress in Inorganic Chemistry, Vol. 49, K. Karlin, Ed., John Wiley & Sons, Inc., New York, 2001, pp. 113-168; Takazaki, Y. et al. (2003) "A Honeycomb Network Of A Paddlewheel-Type Dirhodium Complex In Two Oxidation States And Pinning Of The Oxidation States," Chem. Lett. 32(2):120; and Chifotides, H. T. et al. (2005) "Interactions of Metal-Metal-Bonded Antitumor Active Complexes with DNA Fragments and DNA," Acc. Chem. Res. 38:146-156.

The dirhodium carboximate class of dirhodium (II,II) "paddlewheel" complexes are used for enatioselective carbene transformations (e.g., cyclopropanation, cyclopropenation, and insertion into activated carbon-hydrogen bonds), and are discussed by Doyle, M. P. et al. (1993) "Dirhodium (II) Tetrakis(Carboxamidates) with Chiral Ligands. Structure and Selectivity in Catalytic Metal Carbene Transformations," J. Am. Chem. Soc. 115:9968-9978; Doyle, M. P. et al. (1995) "Highly Enantioselective Route to β-Lactams via Intramolecular C—H Insertion Reactions of Diazoacetylazacyclo-alkanes Catalyzed by Chiral Dirhodium(II) Carboxamidates," Synlett 1075-1076; Doyle, M. P. (1995) "Enantiomer Differentiation in Intramolecular Carbon-Hydrogen Insertion Reactions of Racemic Secondary Alkyl Diazoacetates Catalyzed by Chiral Dirhodium(II) Carboxamidates," Russ. Chem. Bull. 44:1729-1734; Doyle, M. P. et al. (1995) "Enhancement of Enantiocontrol/Diastereocontrol in Catalytic Intramolecular Cyclopropanation and Carbon-Hydrogen Insertion Reactions of Diazoacetates with Rh2(4S-MP-PIM)4" Tetrahedron Lett. 36:7579-7582; Doyle, M. P. et al. (1995) "Optimization of Enantiocontrol for Carbon-Hydrogen Insertion with Chiral Dirhodium(II) Carboxamidates. Synthesis of Natural Dibenzylbutyrolactone Lignans from 3-Aryl-1-propyl Diazoacetates in High Optical Purity," J.

Org. Chem. 60:6654-6655; Doyle, M. P. et al. (1996) "*Highly Enantioselective Intramolecular Cyclopropanation Reactions of N-Allylic-N-methyldiazoacetamides Catalyzed by Chiral Dirhodium(II)Carboxamidates*," J. Org. Chem. 61:2179-2184 (1996); Doyle, M. P. et al. (1996) "*Chiral Dirhodium Carboxamidates. Catalysts for Highly Enantioselective Syntheses of Lactones and Lactams*," Aldrichimica Acta 29(1):3-11; Bode, J. W. et al. (1996) "*Intramolecular Regioselective Insertion into Unactivated Prochiral Carbon-Hydrogen Bonds with Diazoacetates Catalyzed by Chiral Dirhodium(II)Carboxamidates. Highly Enantioselective Total Synthesis of Natural Lignan Lactones*," J. Org. Chem. 61:9146-9155; Doyle, M. P. et al. (1997) "*Highly Enantioselective Oxonium Ylide Formation and Stevens Rearrangement Catalyzed by Chiral Dirhodium(II) Carboxamidates*," Tetrahedron Lett. 38:4367-4370; Roos, G. H. P. et al. (1998) "*Synthesis, Structure, and Reactivity of a Novel Series of Diastereomeric Dirhodium(II) TetraCarboxamidates. Catalysts for Asymmetric Diazoacetate Transformations*," Aust. J. Chem. 51:1-8; Doyle, M. P. et al. (1998) "*Recent Advances in Asymmetric Catalytic Metal Carbene Transformations*," Chem. Rev. 98:911-935; Doyle, M. P. et al. (1998) "*Enantiocontrol in the Generation and Diastereoselective Reactions of Oxonium Ylides Catalyzed by Chiral Dirhodium(II) Carboxamidates. Metal-Stabilized Ylides as Reaction Intermediates*," J. Am. Chem. Soc. 120:7653-7654; Doyle, M. P. et al. (2000) "*Dirhodium(II) Tetrakis[methyl 2-oxaazetidine-4-carboxylate]: A Chiral Dirhodium(II) Carboxamidate of Exceptional Reactivity and Selectivity*," Organic Lett. 2:1145-1147; Doyle, M. P. et al. (2000) "*Optimization of Enantiocontrol in cis-Selective Cyclopropanation Reactions Catalyzed by Dirhodium(II) Tetrakis-[alkyl 2-oxaazetidine-4 (S)-carboxylates]*," J. Chem. Soc. Chem. Commun. 867-868; Doyle, M. P. et al. (2001) "*Reactivity Enhancement for Chiral Dirhodium(II) Tetrakis (Carboxamidates)*," Adv. Synth. Cat. 343(1):112-117; Doyle, M. P. et al. (2001) "*A New Class of Chiral Lewis Acid Catalysts for Highly Enantioselective Hetero-Diels-Alder Reactions: Exceptionally High Turnover Numbers from Dirhodium(II) Carboxamidates*," J. Am. Chem. Soc. 123:5366-5367; Doyle, M. P. et al. (2001) "*High Selectivity from Configurational Match/Mismatch in Carbon-Hydrogen Insertion Reactions of Steroidal Diazoacetates Catalyzed by Chiral Dirhodium(II) Carboxamidates*," J. Org. Chem. 66:8112-8119; Doyle, M. P. et al. (2002) "*Highly Selective Synthesis of a 2-Deoxyxylolcatam via Enantioselective Carbon-Hydrogen Insertion Reactions Using Chiral Dirhodium(II) Carboxamidates*," Adv. Synth. Cat. 344:91-95; Doyle, M. P. et al. (2002) "*Enantioselective Carbon-Hydrogen Insertion is an Effective and Efficient Methodology for the Synthesis of (R)-(-)-Baclofen*," Chirality 14:169-172; Doyle, M. P. et al. (2002) "*Total Synthesis of (S)-(+)-Imperanene. Effective use of Regio-and Enantioselective Intramolecular Carbon-Hydrogen Insertion Reactions Catalyzed by Chiral Dirhodium(II) Carboxamidates*," J. Org. Chem. 67:2954-2959; and by Doyle, M. P. et al. (2002) "*Preparation and Catalytic Properties of Immobilized Chiral Dirhodium(II) Carboxamidates*," Organometallics 21:1747-1749).

The catalytic transformations of are summarized below and in FIG. 1:

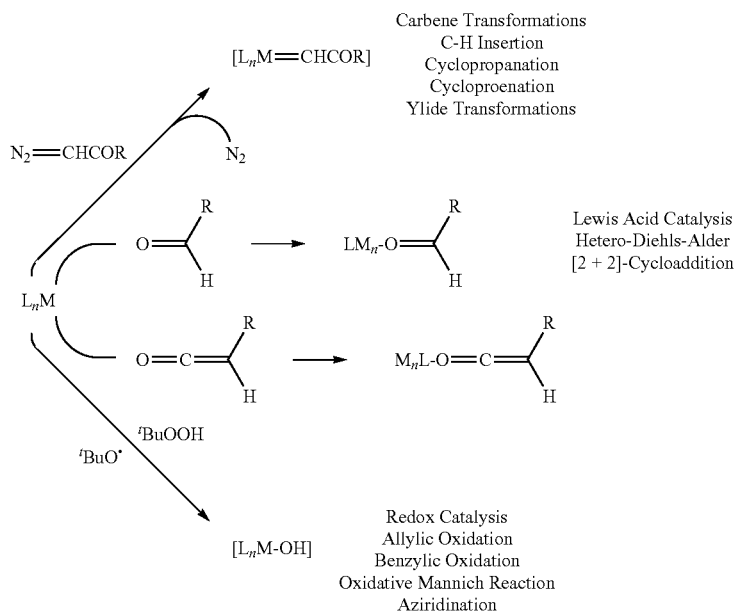

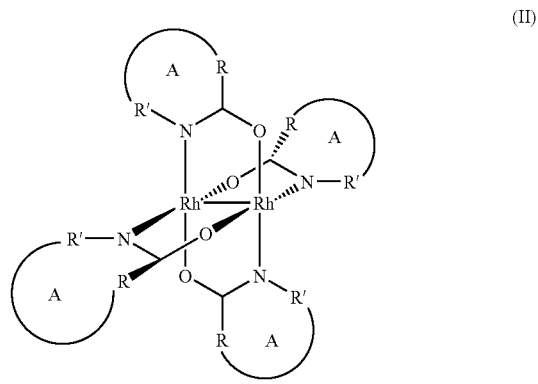

Of particular relevance to the present invention is the dirhodium carboximate class of dirhodium (II,II) "paddlewheel" complexes having the general structure (II):

(II)

wherein A is a ring structure involving R and R' that may be substituted or unsubstituted.

To facilitate the illustration of the dirhodium(II,II) "paddlewheel" compounds of the present invention, such molecules are typically represented herein by showing only one of their four "paddlewheel" A arms and omitting the structures of their remaining three "paddlewheel" A arms. Thus, for example, structures (III) and (VIII) illustrate the same compound. It is, however, to be understood that the unbonded bonds of the rhodium atoms in such depictions are bonded to unshown A moieties. As will be appreciated, the bond lengths and angles in all of the depicted structures herein are not shown to scale. Exemplary dirhodium carboxamidates are shown below, and may be chiral or achiral, as shown in Table 1.

TABLE 1

Exemplary Dirhodium Carboximates (I)

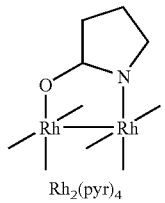

Rh$_2$(pyr)$_4$ (II)

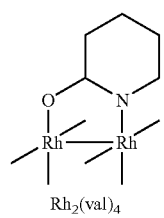

Rh$_2$(val)$_4$ (III)

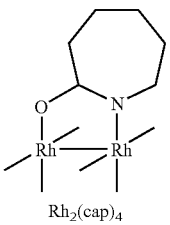

Rh$_2$(cap)$_4$
(Rh$_2$L$_4$)
(dirhodium(II, II) Caprolactamate)

(IV)

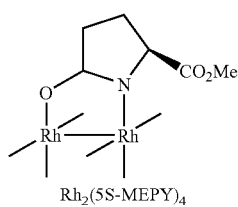

Rh$_2$(5S-MEPY)$_4$ (V)

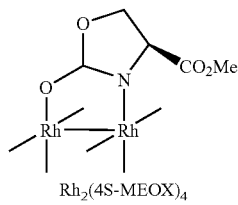

Rh$_2$(4S-MEOX)$_4$

TABLE 1-continued

Exemplary Dirhodium Carboximates (VI)

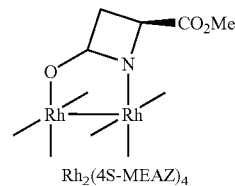

Rh$_2$(4S-MEAZ)$_4$ (VII)

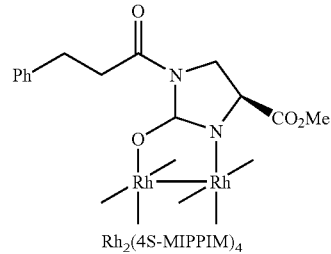

Rh$_2$(4S-MIPPIM)$_4$

Particularly preferred are dirhodium(II,II) carboxamidates paddlewheel complexes that comprise seven-membered rings, such as dirhodium(II,II) caprolactamate (VII), and its derivatives and analogues.

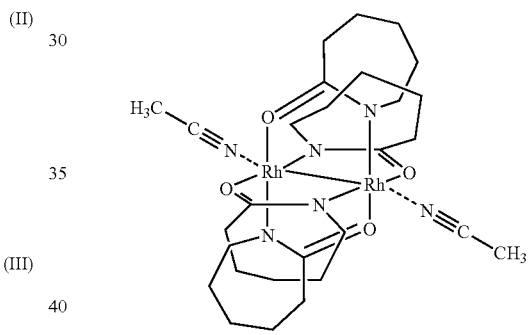

Dirhodium(II,II) Caprolactamate as its
bis-acetonitrile Complex (VIII)

Dirhodium(II,II) caprolactamate (referred to herein as "Rh$_2$(cap)$_4$") is the preferred allylic oxidation catalyst of the present invention. Rh$_2$(cap)$_4$ exhibits a shallow redox potential ($E_{1/2}$=11 mV); Rh$_2$(cap)$_4 \rightarrow$Rh$_2$(cap)$_4^+$<1 kcal/mol (Doyle, M. P. et al. (2001) In: *Progress in Inorganic Chemistry*; volume 49:113, Karlin, K., Ed; Wiley: N.Y.). Dirhodium(II,II) caprolactamate has been found to perform admirably as a catalyst for allylic oxidation (Catino, A. J. et al. (2004) "*Dirhodium (II) Caprolactamate: An Exceptional Catalyst for Allylic Oxidation,*" J. Am. Chem. Soc. 126: 13622-13623). Its effectiveness is derived in part from its ability to undergo facile atom-transfer redox chemistry because of its low one-electron oxidation potential. Rh$_2$(cap)$_4$ has additionally been shown to be a useful catalyst for benzylic oxidation (Catino, A. J. et al. (2005) Org. Lett., 7(23): 5167-5170), enamide/enol oxidation and the oxidative Mannich Reaction (Catino, A. J. et al. (2006) J. Amer. Chem. Soc. 128:5648-5649). The catalyst has been shown to exhibit unprecedented turnover number and frequency and complete selectivity under anhydrous conditions (although tolerant of air and moisture), reacting 1-methylcyclohexene to 3-methylcyclohex-2-enone (yield=89%; tof=45 min$^{-1}$) in 20 minutes at room temperature. in the presence of Rh$_2$(cap)$_4$ (0.1 mol %), $^t$BuOOH (5 equivalents), CHCl$_2$ (Catino, A. J. et al. (2004) "Dirhodium(II) Caprolactamate: An Exceptional Catalyst for Allylic Oxidation," J. Am. Chem. Soc. 126: 13622-13623).

Dirhodium caprolactamate, Rh$_2$(cap)$_4$, has been found to be a highly effective catalyst for allylic oxidations by TBHP (Catino, A. J. et al. (2004) "Dirhodium(II) Caprolactamate: An Exceptional Catalyst for Allylic Oxidation," J. Am. Chem. Soc. 126:13622-13623):

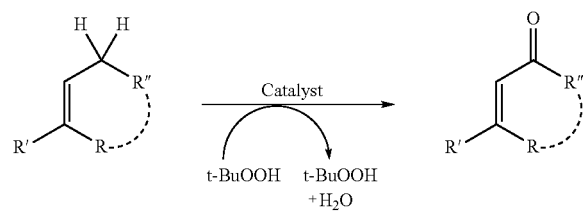

This methodology has been shown to be useful for highly selective allylic oxidations with Δ$^5$-steroidal alcohols (Choi, H. et al. (2007) "Optimal TBHP Allylic Oxidation of Δ$^5$-Steroids Catalyzed by Dirhodium Caprolactamate," Org. Lett. 9:5349-5352). In the course of studies on the oxidation of cycloalkenes, it was observed that those substrates bearing electron-withdrawing substituents were more difficult to oxidize than those with electron-donating substituents. A similar inhibition was reported in studies of TBHP oxidations of α,β-enones to 1,4-enediones facilitated by Pearlman's catalyst [20% Pd(OH)$_2$ on carbon] (Yu, J.-Q. et al. (2003) "A Mild, Catalytic, and Highly Selective Method for the Oxidation of α,β-Enones to 1,4-Enediones, J. Am. Chem. Soc. 125:3232-3233). Substrates having electron-withdrawing substituents generally require greater amounts of TBHP to reach 100% conversion and, with Rh$_2$(cap)$_4$, (Catino, A. J. et al. (2004) "Dirhodium(II) Caprolactamate: An Exceptional Catalyst for Allylic Oxidation," J. Am. Chem. Soc. 126: 13622-13623) require higher catalyst loading.

Tert-Butyl Hydroperoxide

As indicated above, allylic oxidations are of fundamental importance in synthetic organic chemistry, and a variety of reagents have been used for this transformation (Chen, M. S. et al. (2004) "A Sulfoxide-Promoted, Catalytic Method for the Regioselective Synthesis of Allylic Acetates from Monosubstituted Olefins via C—H Oxidation," J. Am. Chem. Soc. 126:1346-1347; Delcamp, J. H. et al. (2006) "Sequential Hydrocarbon Functionalization: Allylic C—H Oxidation/Vinylic C—H Acylation," J. Am. Chem. Soc. 128:15076-15077; Arends, I.W.C. E. et al. (2004) In RUTHENIUM CATALYSTS AND FINE CHEMISTRY; Bruneau, C. et al. Eds.; Springer-Verlag: Heidelberg, Del.). Although stoichiometric selenium dioxide (Umbreit, M. A. et al. (197) "Allylic Oxidation Of Olefins By Catalytic And Stoichiometric Selenium Dioxide With Tert-Butyl Hydroperoxide," J. Am. Chem. Soc. 99:5526-5528; Rabjohn, N. (1976) "Selenium Dioxide Oxidation," Org. React. 24:261-415; Crich, D. et al. (2004) "Catalytic Allylic Oxidation with a Recyclable, Fluorous Seleninic Acid," Org. Lett. 6:775-777; Zeni, G. et al. (2003) "A Convenient Preparation Of Chalcogenoenynes From β-Bromovinyl Ketene Chalcogenoacetals," Synlett 12:1880-1882) and chromium (VI) (Shing, T. M. K. et al. (2005) "Total Synthesis Of (−)-Samaderine Y From (S)-(+)-Carvone," Angew. Chem. Int. Ed. 44:7981-7984; Hua, Z. et al. (2005) "The Synthesis and Preliminary Biological Evaluation of a Novel Steroid with Neurotrophic Activity: NGA0187," J. Org. Chem. 70:9849-9856; Salmond, W. G. et al. (1978) "Allylic Oxidation With 3,5-Dimethylpyrazole. Chromium Trioxide Complex Steroidal .DELTA.5-7-Ketones," J. Org. Chem. 43:2057-2059) reagents have long been used to convert the methylene adjacent to a carbon-carbon double bond to a carbonyl group, the most promising oxidant, applicable to catalytic methods, is tert-butyl hydroperoxide (TBHP) [1,1-dimethyl hydroperoxide; 2-hydroperoxy-2-methylpropane] (Rothenberg, G. et al. (1998) "Pyridines As Bifunctional Co-Catalysts In The CrO3-Catalyzed Oxygenation Of Olefins By T-Butyl Hydroperoxide," J. Mol. Catal. A: Chemical 136:253-262; Jurado-Gonzalez, M. et al. (2003) "Allylic and Benzylic Oxidation Using Cobalt(II) Alkyl Phosphonate Modified Silica," Tetrahedron Lett. 44:4283-4286; Arsenou, E. S. et al. (2003) "Optimization Of The Allylic Oxidation In The Synthesis Of 7-Keto-±D5-Steroidal Substrates," Steroids 68:407-414; Yu, J.-Q. et al. (2002) "Diverse Pathways for the Palladium(II)-Mediated Oxidation of Olefins by tert-Butylhydroperoxide," Org. Lett. 4:2727-2730; Yu, J.-Q. et al. (2005) "Pd(OH)$_2$/C-Mediated Selective Oxidation of Silyl Enol Ethers by tert-Butylhydroperoxide, a Useful Method for the Conversion of Ketones to α,β-Enones or β-Silyloxy-α,β-enones," Org. Lett. 7:1415-1417; Shing, T. K. M. et al. (2006) "Mild Manganese (III) Acetate Catalyzed Allylic Oxidation: Application to Simple and Complex Alkenes," Org. Lett. 8:3149-3151; Blay, G. et al. (2001) "Alkane Oxidation By A Carboxylate-Bridged Dimanganese(III) Complex," Chem. Comm. 11:2102-2104; Salvador, J. A. R. et al. (2001) "The Allylic Oxidation Of Unsaturated Steroids By Tert-Butyl Hydroperoxide Using Homogeneous And Heterogeneous Cobalt Acetate," Chem. Commun. 33-35).

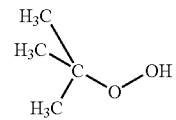

tert-Butyl Hydroperoxide (TBHP)

In addition to the use of palladium catalysis for allylic oxidation by TBHP (Yu, J.-Q. et al. (2003) "A Mild, Catalytic, and Highly Selective Method for the Oxidation of α,β-Enones to 1,4-Enediones, J. Am. Chem. Soc. 125:3232-3233), copper (II) and iron(III) salts have also been employed (Bravo, A. et al. (1997) "Ingold-Fischer "Persistent Radical Effect", Solvent Effect, and Metal Salt Oxidation of Carbon-Centered Radicals in the Synthesis of Mixed Peroxides from tert-Butyl Hydroperoxide," J. Org. Chem. 62:3849-3857; Caudle, M. T. et al. (1996) "Mechanism for the Homolytic Cleavage of Alkyl Hydroperoxides by the Manganese(III) Dimer Mn$^{III}_2$(2-OHsalpn)$_2$," Inorg. Chem. 35:3577-3584) as have chromium (VI) (Fousteris, M. A. et al. (2006) "Improved Chromium-Catalyzed Allylic Oxidation Of Δ5-Steroids With T-Butyl Hydroperoxide," J. Mol. Catal. A: Chem. 250:70-74), manganese(III) (Shing, T. K. M. et al. (2006) "Mild Manganese (III) Acetate Catalyzed Allylic Oxidation: Application to Simple and Complex Alkenes," Org. Lett. 8:3149-3151), copper iodide (Arsenou, E. S. et al. (2003) "Optimization Of The Allylic Oxidation In The Synthesis Of 7-Keto-±D5-Steroidal Substrates," Steroids 68:407-414), cobalt acetate (Salvador, J. A. R. et al. (2001) "The Allylic Oxidation Of Unsaturated Steroids By Tert-Butyl Hydroperoxide Using Homogeneous And Heterogeneous Cobalt Acetate," Chem. Commun. 33-35), and ruthenium(III) (Miller, R. A. et al. (1996) "*A Ruthenium Catalyzed Oxidation Of Steroidal Alkenes To Enones,*" Tetrahedron Lett. 37:3429-3432). Although the tert-butylperoxy radical is the most likely hydrogen abstraction agent (Blanksby, S. J. et al. (2003) "*Bond Dissociation Energies Of Organic Molecules,*" Acc. Chem. Res. 36:255-263; Catino, A. J. et al. (2004) "*Dirhodium(II) Caprolactamate: An Exceptional Catalyst for Allylic Oxidation,*" J. Am. Chem. Soc. 126:13622-13623; Choi, H. et al. (2007) "*Optimal TBHP Allylic Oxidation of $\Delta^5$-Steroids Catalyzed by Dirhodium Caprolactamate,*" Org. Lett. 9:5349-5352), the possibility of oxo-metal involvement, especially with ruthenium catalysts (Ballini, R. et al. (1996) "*Convenient Synthesis of (E)-Non-3-ene-2,5-dione, an Important Component Isolated from the Fire Bee Trigona tataira*" Liebigs Ann. 11: 1879-1880) persists.

Selectivity for allylic oxidation by TBHP is due to the ability of the tert-butylperoxy radical to remove a hydrogen atom from the activated site having the lowest carbon-hydrogen bond dissociation energy (Blanksby, S. J. et al. (2003) "*Bond Dissociation Energies Of Organic Molecules,*" Acc. Chem. Res. 36:255-263). However, application of this methodology for allylic oxidation with compounds of increasing complexity has been demonstrated in very few cases.

Another feature of allylic oxidations using TBHP is the frequent use of the oxidant in decane or benzene (Yu, J.-Q. et al. (2002) "*Diverse Pathways for the Palladium (II)-Mediated Oxidation of Olefins by tert-Butylhydroperoxide,*" Org. Lett. 4:2727-2730; Yu, J.-Q. et al. (2005) "*Pd(OH)$_2$/C-Mediated Selective Oxidation of Silyl Enol Ethers by tert-Butylhydroperoxide, a Useful Method for the Conversion of Ketones to $\alpha,\beta$-Enones or $\beta$-Silyloxy-$\alpha,\beta$-enones,*" Org. Lett. 7:1415-1417; Shing, T. K. M. et al. (2006) "*Mild Manganese(III) Acetate Catalyzed Allylic Oxidation: Application to Simple and Complex Alkenes,*" Org. Lett. 8:3149-3151; Blay, G. et al. (2001) "*Alkane Oxidation By A Carboxylate-Bridged Dimanganese(III) Complex,*" Chem. Comm. 11:2102-2104; Salvador, J. A. R. et al. (2001) "*The Allylic Oxidation Of Unsaturated Steroids By Tert-Butyl Hydroperoxide Using Homogeneous And Heterogeneous Cobalt Acetate,*" Chem. Commun. 33-35; Catino, A. J. et al. (2004) "*Dirhodium(II) Caprolactamate: An Exceptional Catalyst for Allylic Oxidation,*" J. Am. Chem. Soc. 126:13622-13623; Yu, J.-Q. et al. (2003) "*A Mild, Catalytic, and Highly Selective Method for the Oxidation of $\alpha,\beta$-Enones to 1,4-Enediones,*" J. Am. Chem. Soc. 125:3232-3233; Salvador, J. A. R. et al. (2005) "*Bismuth-Catalyzed Allylic Oxidation Using t-Butyl Hydroperoxide,*" Tetrahedron Lett. 46:2581-2584) as an anhydrous solution, instead of the much safer and less expensive 70% TBHP in water (T-HYDRO®). TBHP reactions were conducted in decane based on a belief that hydrolysis of carboxamidate ligands on the Rh$_2$(cap)$_4$ catalyst would be avoided under these conditions (Catino, A. J. et al. (2004) "*Dirhodium(II) Caprolactamate: An Exceptional Catalyst for Allylic Oxidation,*" J. Am. Chem. Soc. 126:13622-13623). However, it was observed that T-HYDRO® catalyzed effective allylic oxidations in reactions catalyzed by Rh$_2$(cap)$_4$ (Choi, H. et al. (2007) "*Optimal TBHP Allylic Oxidation of $\Delta^5$-Steroids Catalyzed by Dirhodium Caprolactamate,*" Org. Lett. 9:5349-5352) and McLaughlin, E. C. et al. described propargylic oxidations that employed water as the reaction solvent (McLaughlin, E. C. et al. (2008) "*Propargylic Oxidations Catalyzed by Dirhodium Caprolactamate in Water: Efficient Access to $\alpha,\beta$-Acetylenic Ketones,*" J. Org. Chem. 73:4317-4319). The catalytically active rhodium species remains intact for sufficient periods under these conditions.

One aspect of the invention thus relates to the recognition that tert-Butyl hydroperoxide ("TBHP") oxidizes alkenes at their allylic position to unsaturated carbonyl compounds and arenes at their benzylic position when these reactions are catalyzed by dirhodium(II) carboxamidates and conducted in the presence of water. These oxidations form the carbonyl compound cleanly and in moderate to high yield and are particularly applicable to sterols, terpenes and unsaturated fatty acids, which are not oxidized by the same procedure in non-aqueous media. One advantage of the present invention lies in the large number of combination of conditions (oxidant, media, catalyst, temperature, method of addition) that are favorable to these otherwise difficult to achieve oxidations.

Although, as discussed above, TBHP is widely used as a chemical oxidant, prior to the present invention it had been used in an aqueous solvent to mediate allylic oxidation only as a co-solvent with cyclohexane and in a reaction catalyzed by ruthenium trichloride (Miller, R. A. et al. (1996) "*A Ruthenium Catalyzed Oxidation Of Steroidal Alkenes To Enones,*" Tetrahedron Lett. 37:3429-3432). Additionally, whereas such reactions required 10 molar equivalents of TBHP, the procedures of the present invention permit allylic oxidation to occur using less than 10 molar equivalents of TBHP, still more preferably, 9 or fewer molar equivalents of TBHP, still more preferably, 8 or fewer molar equivalents of TBHP, still more preferably, 7 or fewer molar equivalents of TBHP, still more preferably, 6 or fewer molar equivalents of TBHP, still more preferably, 5 or fewer molar equivalents of TBHP, and still more preferably, 4-5 molar equivalents of TBHP.

Without intending to be bound thereby, it is believed that the limitation in prior work to anhydrous conditions appears to be due to a perception that the required catalyst would be destroyed or inhibited by contact with water. The invention reflects the unexpected finding that dirhodium(II) carboxamidate catalysts are stable to hydrolysis by water at temperatures preferably of from about 20° C. to about 60° C., more preferably from about 20° C. to about 50° C., more preferably from about 20° C. to about 40° C., and most preferably from room temperature (22-25° C.) to 40° C. during the course of oxidation.

The reaction mechanism involves the consumption of oxygen and is characterized by the absence in the final product mixtures of alcohol intermediates to ketones and the non-oxidation of secondary alcohols under the same reaction conditions. The reaction mechanism may be depicted as follows with cyclohexene as the substrate being oxidized:

t-BuO• + t-BuOOH ⟶ t-BuOH + t-BuOO•

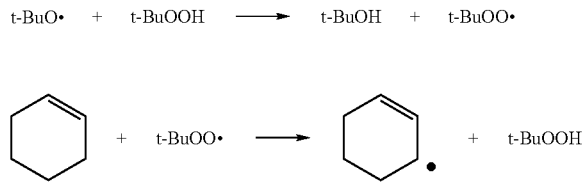

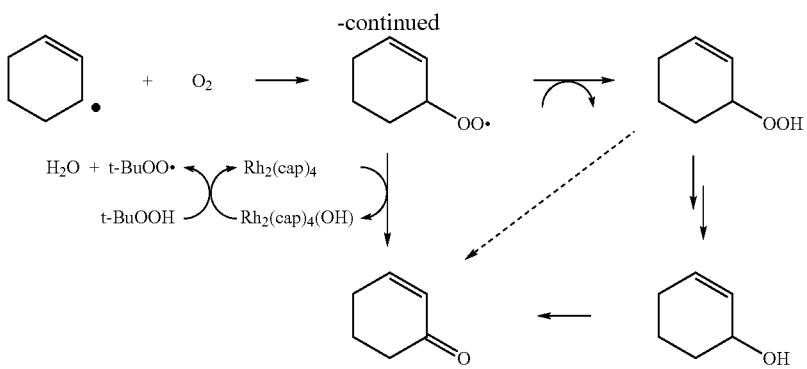

Preferred Reactions Conditions

The oxidation reactions of the present invention are preferably conducted by incubating substrate in an organic solvent (e.g., 1,2-dichloroethane ("DCE") and dichloromethane) (Catino, A. J. et al. (2005) Org. Lett., 7(23):5167-5170). tert-Butyl hydroperoxide in an aqueous solution (particularly T-HYDRO® (a TBHP 70% aqueous solution; Aldrich Chemical) is provided in excess (preferably 2-10, more preferably 4-8, and most preferably 4-5 moles per mole of substrate (molar equivalents or mol %). A dirhodium (II,II) "paddlewheel" complex, most preferably dirhodium(II) carboxamidate is provided (preferably at 0.1-1.0 mol %, more preferably at 0.2-0.8 mol %, more preferably at 0.4-0.6 mol %, and most preferably at about 0.5 mol %). The reaction is then adjusted to a temperature preferably of between about 20° C. to about 60° C., more preferably between about 20° C. to about 50° C., still more preferably between about room temperature (22-25° C.) to about 40° C., and most preferably to about 40° C. during the course of oxidation. The reaction is permitted to occur over a period of several hours (e.g., 2, 8, 16, 24 hours or longer), under the desired degree of yield has been obtained.

Having now generally described the invention, the same will be more readily understood through reference to the following examples, which are provided by way of illustration and are not intended to be limiting of the present invention unless specified.

EXAMPLES

Example 1

Anhydrous Allylic Oxidation

As shown by Catino, A. J. et al., (2004) ("*Dirhodium(II) Caprolactamate: An Exceptional Catalyst for Allylic Oxidation*," J. Am. Chem. Soc. 126:13622-13623), under anhydrous conditions, $Rh_2(cap)_4$ is capable of mediating efficient allylic oxidation. The yields of products for several exemplary compounds produced via anhydrous synthesis are shown in Table 2.

TABLE 2

Anhydrous Allylic Oxidation

General reaction: cycloalkene + $Rh_2(cap)_4$ (0.1 mol %), $K_2CO_3$ (50 mol %), $^tBuOOH$ (5.0 equiv.), $CH_2Cl_2$, 1 hour → cycloalkenone (n = 0, 1, 2)

| Entry | Substrate | Product | % Yield |
|---|---|---|---|
| 1 | cyclohexene | 2-cyclohexen-1-one | 60 |
| 2 | 4-tert-butylcyclohexene | 5-tert-butyl-2-cyclohexen-1-one | 94 |
| 3 | 4-phenylcyclohexene | 5-phenyl-2-cyclohexen-1-one | 77 |
| 4 | methyl cyclohex-1-ene-1-carboxylate | methyl 3-oxocyclohex-1-ene-1-carboxylate | 92 |
| 5 | 4-nitrocyclohexene | 5-nitro-2-cyclohexen-1-one | 64* |

TABLE 2-continued

| # | Substrate | Product | Yield |
|---|---|---|---|
| 6 | H₃C-cyclohexene | 3-methylcyclohex-2-enone | 89 |
| 7 | 1-acetylcyclopentene (H₃C-C(=O)-) | 3-acetylcyclopent-2-enone | 86 |
| 8 | methyl cyclopentene-1-carboxylate (H₃CO-C(=O)-) | methyl 4-oxocyclopent-2-ene-1-carboxylate (H₃CO-C(=O)-) | 79 |
| 9 | cyclohept-2-enone | cyclohept-2-ene-1,4-dione | 83* |
| 10 | dioxolane-spiro-cyclopentene | dioxolane-spiro-cyclopentenone | 61* |

Table Notes:
Reactions were performed using Rh₂(cap)₄ (0.1 mol %), K₂CO₃ (50 mol %), ᵗ-BuOOH (5.0 equiv); CH₂Cl₂, 1 hour
*1 mol % Rh₂(cap)₄ and additional reaction time required Example 2

Optimization of Aqueous Allylic Oxidation Conditions of Non-Steroidal Compounds

In order to determine aqueous allylic oxidation reaction conditions for non-steroidal compounds, trans-3-nonene-2-one, whose fire bee toxin (Russell, G. A. (1957) "*Deuterium-isotope Effects in the Autoxidation of Aralkyl Hydrocarbons. Mechanism of the Interaction of Peroxy Radicals*," J. Am. Chem. Soc. 79:3871-3877; Caudle, M. T. et al. (1996) "*Mechanism for the Homolytic Cleavage of Alkyl Hydroperoxides by the Manganese(III) Dimer Mn$^{III}_2$(2-OHsalpn)$_2$*," Inorg. Chem. 35:3577-3584) product trans-3-nonene-2,5-dione (1) has been previously prepared by anhydrous allylic oxidation (Catino, A. J. et al. (2004) "*Dirhodium(II) Caprolactamate: An Exceptional Catalyst for Allylic Oxidation*," J. Am. Chem. Soc. 126:13622-13623) was selected for optimization:

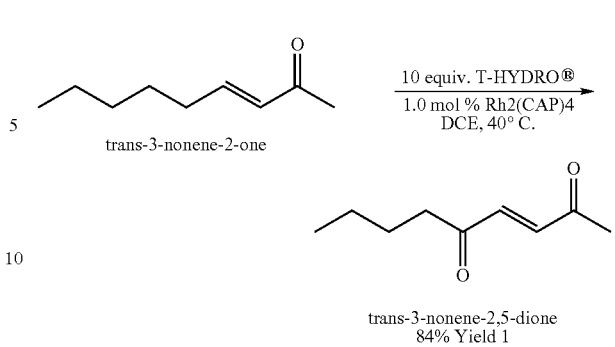

trans-3-nonene-2-one → trans-3-nonene-2,5-dione
84% Yield 1

Figure 2:
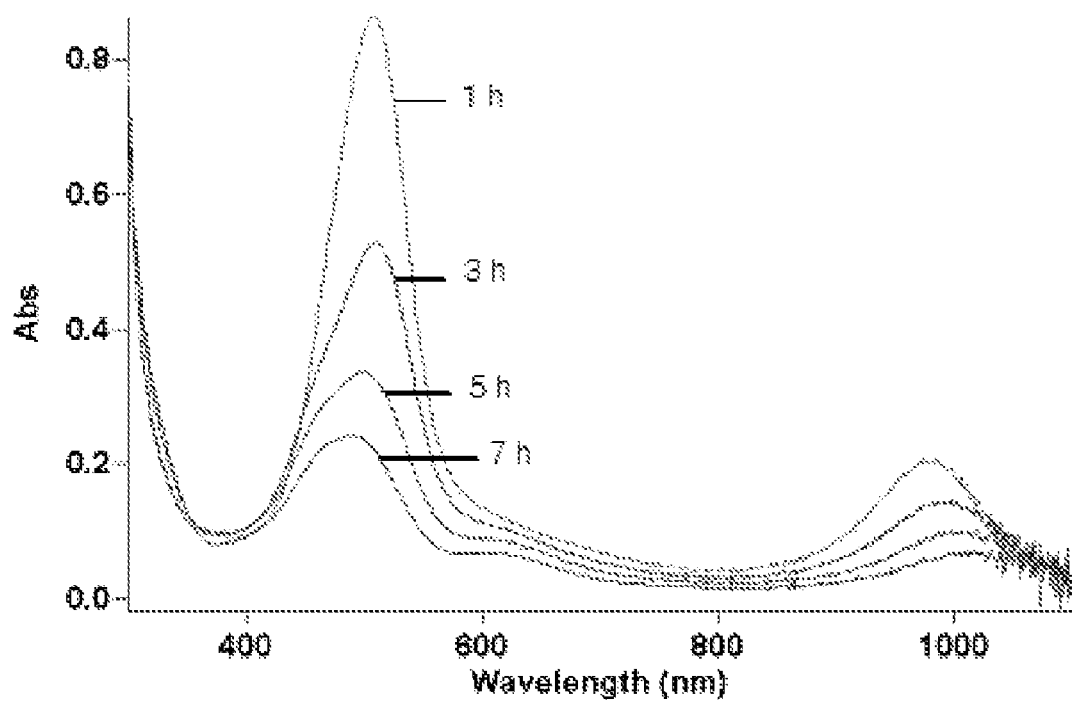
FIG. 2 shows Dirhodium (II,III) caprolactamate visible spectrum as a function of time (1, 3, 5, and 7 h): TBHP (0.27 M) in DCE with 1.0 mol % $Rh_2(cap)_4$ without olefinic substrate. Note that dirhodium (II,III) caprolactamate ($\lambda_{max}$ 507 and 974 nm) is clearly visible even after 5 h and that dirhodium (II,II) caprolactamate ($\lambda_{max}$ 607 nm) becomes visible as the reaction proceeds.

Using T-HYDRO® as the oxidant and Rh$_2$(cap)$_4$ as the catalyst at 40° C., various solvents were examined for suitability. 1,2-Dichloroethane (DCE), nitromethane, and water all led to comparable conversions to product (1) after 16 hours when 8 equivalents of TBHP were employed. In contrast to previous reports of catalytic TBHP oxidations under anhydrous conditions (Yu, J.-Q. et al. (2002) "*Diverse Pathways for the Palladium(II)-Mediated Oxidation of Olefins by tert-Butylhydroperoxide*," Org. Lett. 4:2727-2730; Yu, J.-Q. et al. (2005) "*Pd(OH)$_2$/C-Mediated Selective Oxidation of Silyl Enol Ethers by tert-Butylhydroperoxide, a Useful Method for the Conversion of Ketones to α,β-Enones or β-Silyloxy-α,β-enones*," Org. Lett. 7:1415-1417; Blanksby, S. J. et al. (2003) "*Bond Dissociation Energies Of Organic Molecules*," Acc. Chem. Res. 36:255-263) the addition of weak bases such as sodium bicarbonate, pyridine, or triethylamine lowered percent conversions. Two factors limited the efficiency of this allylic oxidation: (1) the slow rate of oxidation of the substrate relative to radical chain decomposition of TBHP ($k_P$/$k_D$, Scheme 1) (Timmons, D. et al. In METAL BONDS BETWEEN METAL ATOMS, 3rd Ed.; Cotton, F. A. et al. Eds.; Springer Science and Business Media: New York; (2005) Chapter 13) and (2) the decrease in the concentration of the catalytically active dirhodium species (FIG. 2). For the former, increasing the number of molar equivalents of TBHP increased percent conversion, and increasing the reaction temperature from room temperature to 40° C. increased the rate of oxidation. For the latter, adding Rh$_2$(cap)$_4$ in two portions, 0.5 mol % to initiate the reaction and the second 0.5 mol % portion after 16 h, ensured complete conversion and high product yield. Subsequent studies revealed that complete conversion could be achieved using as little as 0.1 mol % Rh$_2$(cap)$_4$ if applied twice, each with 5.0 molar equiv of TBHP, after the initial addition (22 and 44 h).

Scheme 1

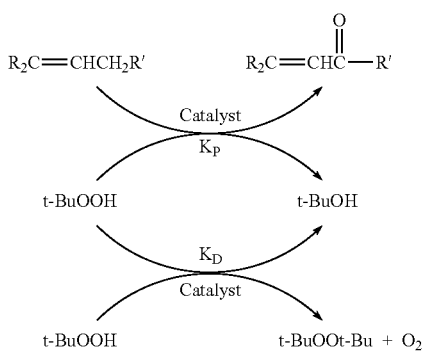

The role of dirhodium caprolactamate in these oxidation reactions is suggested from the spectral observations revealed in FIG. 2. The conversion of $Rh_2(cap)_4$ to its oxidized $Rh(cap)_4RhOH$ form by TBHP has been reported by Choi, H. et al., (2007) "*Optimal TBHP Allylic Oxidation of $\Delta^5$-Steroids Catalyzed by Dirhodium Caprolactamate*," Org. Lett. 9:5349-5352). One aspect of the present invention relates to the recognition that $Rh(cap)_4RhOH$ is converted back to $Rh_2(cap)_4$ via TBHP. The observation of $Rh_2(cap)_4$ in FIG. 2, combined with confirmation of its initial formation and presence throughout the course of oxidation through HPLC analysis, confirms the catalytic role for $Rh_2(cap)_4$ that is described in Scheme 2. Thus, the Example demonstrates that dirhodium caprolactamate is effective and efficient for the production of the tert-butylperoxy radical.

Scheme 2

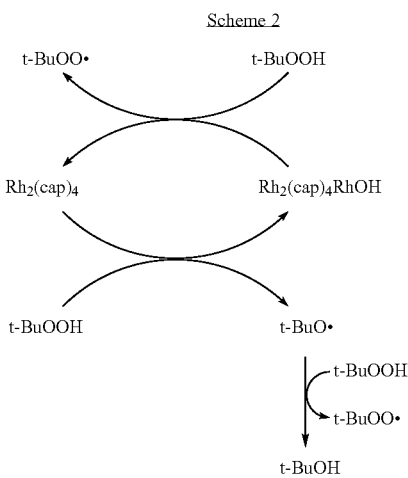

Optimized conditions were selected for oxidation of α,β-unsaturated substrates (0.54 M in DCE) that included initial addition of 0.5 mol % $Rh_2(cap)_4$ and 4.0 or 5.0 equiv T-HYDRO® followed by the same portion of catalyst and oxidant after 16 hours. Reactions were performed at 40° C. and terminated 40 hours after the initial catalyst/oxidant addition. Percent conversion at 16 hours was only half that at 40 hours, and using acetonitrile or nitromethane as solvent resulted in lower conversions than that achieved in DCE. Selected α,β-unsaturated carbonyl compounds were oxidized according to this methodology, and the results are reported in Table 3. Noteworthy are the relatively high yields of oxidized product obtained with acyclic compounds. For example, trans-4-oxo-2-nonenoic acid (3), reported to have antibiotic activity (Pfefferle, C. et al. (1996) "*(E)-4-Oxonon-2-Enoic Acid, An Antibiotically Active Fatty Acid Produced By Streptomyces olivaceus Tü 4018*," J. Antibiotics 49:826-828), is efficiently prepared in one transformation (entry 3), improving upon the previously described multistep syntheses (Ballini, R. et al. (1998) "*Synthesis of (E)-4-Oxonon-2-enoic Acid, a Natural Antibiotic Produced by Streptomyces olivaceus*," J. Nat. Prod. 61:673-674; Shet, J. et al. (2004) "*Domino Primary Alcohol Oxidation-Wittig Reaction: Total Synthesis of ABT-418 and (E)-4-Oxonon-2-enoic Acid*," Synthesis 11:1859-1863; Obrect, D. et al. (1989) "*A New Method for the Preparation of (E)-3-Acylprop-2-enoic Acids*," Helv. Chim. Acta 72:117-122). Oxidation of methyl crotonate under the same conditions yielded monomethyl fumaric acid (entry 8) in modest isolated yield.

Reactions were performed with 1.36 mmol of substrate in 2.5 mL of DCE to which was added 4.0 or 5.0 equiv of TBHP (70% in water) and 0.50 mol % $Rh_2(cap)_4$ and the solution was heated at 40° C. After 16 hours an additional 4.0 or 5.0 equiv of TBHP (70% in water) and 0.50 mol % $Rh_2(cap)_4$ was added, and reaction was continued for an additional 24 hours. Isolated yield after column chromatography; carboxylic acids were purified by recrystallization from ethyl acetate and the mass yield after recrystallation is given.

TABLE 3

Oxidation of α,β-Unsaturated Carbonyl Compounds by T-HYDRO ® Catalyzed by $Rh_2(cap)_4$

| Entry | Substrate | Product | Equiv. TBHP | % Yield |
|---|---|---|---|---|
| 1 | H₃C-(CH₂)₃-CH=CH-C(O)-CH₃ | H₃C-(CH₂)₃-C(O)-CH=CH-C(O)-CH₃ | 10.0<br>8.0 | 84<br>76 |
| 2 | H₃C-(CH₂)₃-CH₂-CH=CH-C(O)-OEt | H₃C-(CH₂)₃-C(O)-CH=CH-C(O)-OEt | 10.0 | 76 |
| 3 | H₃C-(CH₂)₃-CH=CH-C(O)-OH | H₃C-(CH₂)₃-C(O)-CH=CH-C(O)-OH | 10.0 | 87 |

TABLE 3-continued

Oxidation of α,β-Unsaturated Carbonyl Compounds by T-HYDRO ® Catalyzed by $Rh_2(cap)_4$

| Entry | Substrate | Product | Equiv. TBHP | % Yield |
|---|---|---|---|---|
| 4 | (structure: CH$_3$CH=CHCH$_2$C(O)OH) | (structure 4: CH$_3$C(O)CH=CHC(O)OH) | 10.0<br>8.0 | 85<br>82 |
| 5 | (structure: CH$_3$CH=CHCH$_2$C(O)NH$_2$) | (structure 5: CH$_3$C(O)CH=CHC(O)NH$_2$) | 8.0 | 65 |
| 6 | (structure: CH$_3$CH=CHCH$_2$C(O)N(i-Pr)$_2$) | (structure 6: CH$_3$C(O)CH=CHC(O)N(i-Pr)$_2$) | 8.0 | 70 |
| 7 | (cyclohexene-COOH) | (structure 7: 3-oxocyclohex-1-ene-carboxylic acid) | 8.0 | 64 |
| 8 | (structure: CH$_3$CH=CHC(O)OMe) | (structure 8: HOOC-CH=CH-C(O)OMe) | 8.0 | 32 |

Figure 3:
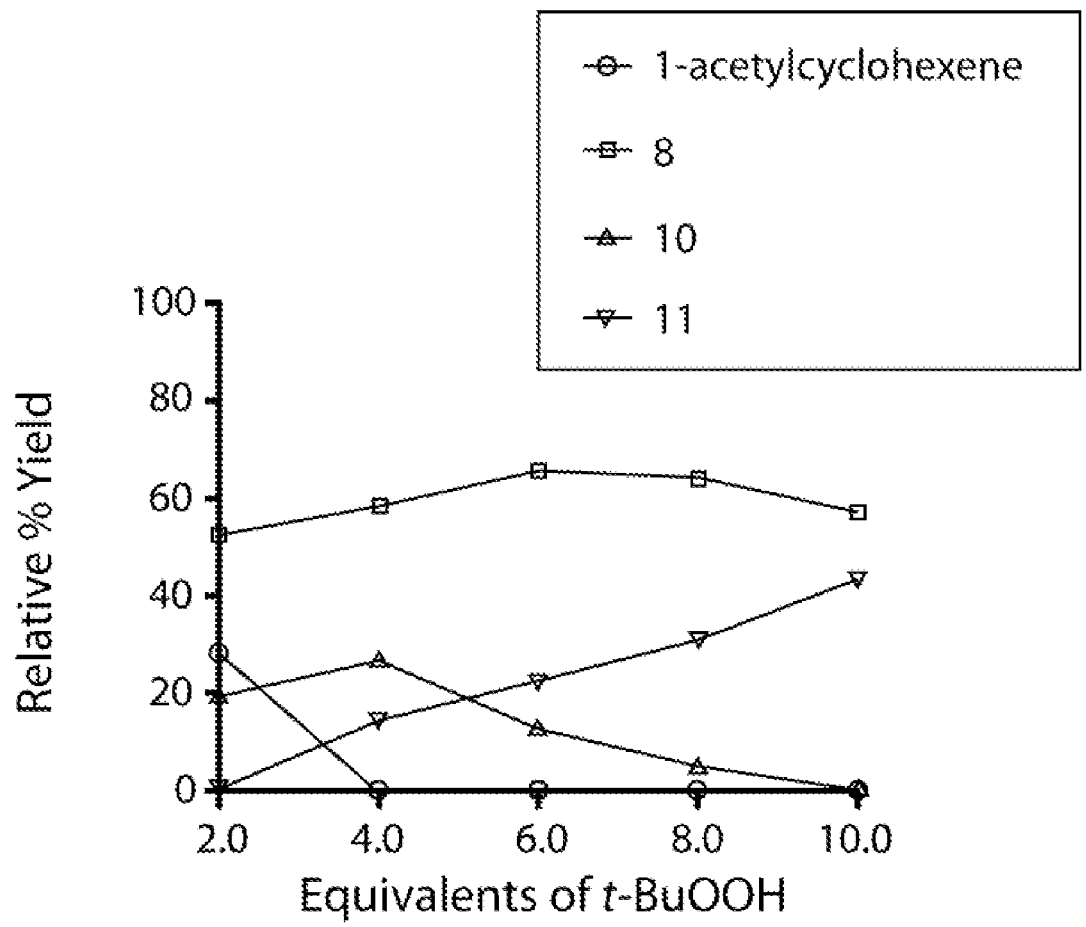
FIG. 3 shows the oxidation of 1-acetylcyclohexene (0.27 M in DCE, 40° C.) by T-HYDRO®, catalyzed by $Rh_2(cap)_4$. The relative yield of oxidation products as a function of molar equivalents of TBHP was determined after 16 hours.

The oxidation reactions reported in Table 3 are remarkably free of by-products. However, while investigating the T-HYDRO® oxidation of 1-acetylcyclohexene (a substrate that was reported to be cleanly oxidized by TBHP in decane using $Rh_2(cap)_4$ aided by potassium carbonate (Blanksby, S. J. et al., (2003) "*Bond Dissociation Energies Of Organic Molecules,*" Acc. Chem. Res. 36:255-263) three unreported mixed peroxides shown in Table 4 (10, 11, and 12) were identified in addition to the previously reported peroxide (13) (Choi, H. et al. (2007) "*Optimal TBHP Allylic Oxidation of $\Delta^5$-Steroids Catalyzed by Dirhodium Caprolactamate,*" Org. Lett. 9:5349-5352) and the desired enedione (9). Two of these mixed peroxides (10 and 11) were revealed during a study of the influence of TBHP molar amount on product formation (FIG. 3); mixed peroxide 12 was isolated from a reaction that employed 0.5 mol % $Rh_2(cap)_4$ and 4.0 molar equivalents TBHP. That enone 11 results from allylic oxidation of 10 is clearly suggested from the data in FIG. 3.

TABLE 4

Reaction Products 9 (3-acetyl-cyclohex-2-enone structure)

10 (3-acetyl-3-(tert-butylperoxy)-cyclohex-1-ene structure, with OOt-Bu group)

TABLE 4-continued

Reaction Products

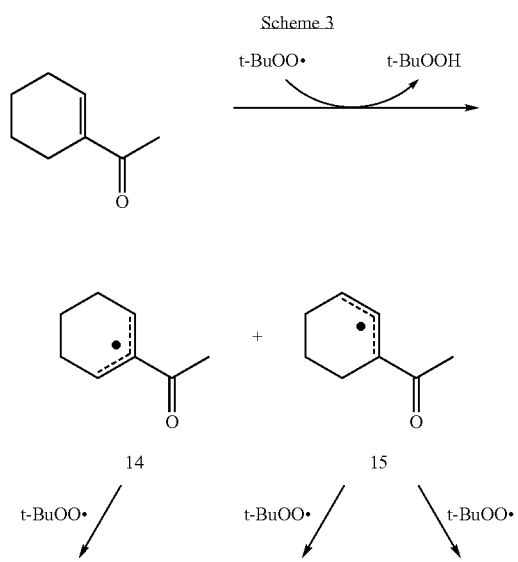

Mixed peroxide 10 is formed in competition with mixed peroxide 13 and enedione 9. Formation of mixed peroxides 10, 11, 12, and 13 is consistent with the generation of intermediate allyl radicals 14 and 15 (Scheme 3) that subsequently react with the tert-butylperoxy radical. As can be seen from overall product formation, intermediate 15 is more prevalent than 14. Conversely, oxidations of cyclohexene derivatives bearing electron-donating substituents at the 1-position (e.g., AcO, tert-butyl) under identical conditions did not form detectable amounts of mixed peroxide products (Catino, A. J. et al. (2004) "*Dirhodium(II) Caprolactamate: An Exceptional Catalyst for Allylic Oxidation,*" J. Am. Chem. Soc. 126:13622-13623).

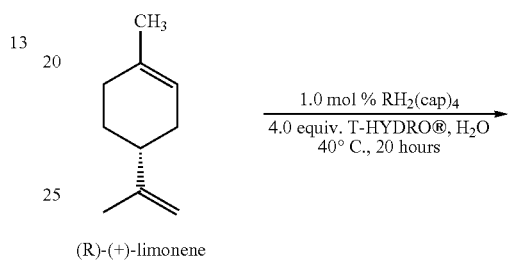

Further support that the pathway described in Scheme 3 is operative in $Rh_2(cap)_4$ catalyzed oxidations by TBHP was demonstrated through oxidation of enantiomerically pure (R)-(+)-limonene with T-HYDRO® in water:

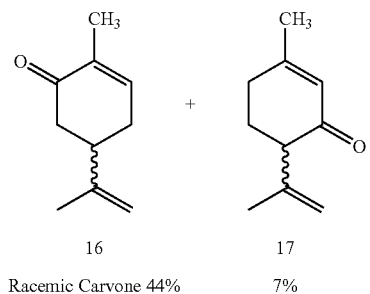

Unlike previous TBHP oxidations of 1-substituted cyclohexenes, from which the dominant product resulted from oxidation at the 3-position (Rothenberg, G. et al. (1998) "*Pyridines As Bifunctional Co-Catalysts In The CrO3-Catalyzed Oxygenation Of Olefins By T-ButylHydroperoxide,*" J. Mol. Catal. A: Chemical 136:253-262; Jurado-Gonzalez, M. et al. (2003) "*Allylic and Benzylic Oxidation Using Cobalt(II) Alkyl Phosphonate Modified Silica,*" Tetrahedron Lett. 44:4283-4286; Arsenou, E. S. et al. (2003) "*Optimization Of The Allylic Oxidation In The Synthesis Of 7-Keto-±D5-Steroidal Substrates,*" Steroids 68:407-414; Yu, J.-Q. et al. (2002) "*Diverse Pathways for the Palladium (II)-Mediated Oxidation of Olefins by tert-Butylhydroperoxide,*" Org. Lett. 4:2727-2730; Yu, J.-Q. et al. (2005) "*Pd(OH)$_2$/C-Mediated Selective Oxidation of Silyl Enol Ethers by tert-Butylhydroperoxide, a Useful Method for the Conversion of Ketones to α,β-Enones or β-Silyloxy-α,β-enones,*" Org. Lett. 7:1415-1417; Shing, T. K. M. et al., (2006) "*Mild Manganese(III) Acetate Catalyzed Allylic Oxidation: Application to Simple and Complex Alkenes,*" Org. Lett. 8:3149-3151; Blay, G. et al. (2001) "*Alkane Oxidation By A Carboxylate-Bridged Dimanganese(III) Complex,*" Chem. Comm. 11:2102-2104; Salvador, J. A. R. et al. (2001) "*The Allylic Oxidation Of Unsaturated Steroids By Tert-Butyl Hydroperoxide Using Homogeneous And Heterogeneous Cobalt Acetate,*" Chem. Commun. 33-35; Blanksby, S. J. et al. (2003) "*Bond Dissociation Energies Of Organic Molecules,*" Acc. Chem. Res.

36:255-263; Catino, A. J. et al. (2004) "*Dirhodium(II) Caprolactamate: An Exceptional Catalyst for Allylic Oxidation*," J. Am. Chem. Soc. 126:13622-13623) the dominant product of the oxidation of (R)-(+)-limonene was racemic carvone (16, 44% isolated yield). The observed carvone 16 arose from hydrogen atom abstraction from the 6-position of limonene to produce a racemic free radical that underwent subsequent transformation. The expected oxidation at the 3-position of limonene, affording isopiperitinone 17, was observed as the minor reaction product (7% isolated yield). Other oxidation products were also formed, but in lower yield than 17, and they were not identified. The preference for hydrogen atom abstraction from the 6-position, rather than from the 3-position, suggests the operation of steric factors. Although allylic oxidations of limonene, other than those by selenium dioxide (e.g., selective oxidation occurs at the 4-position: Wilson, C. A., III et al. (1973) "(+)-*Limonene Oxidation With Selenium Dioxide-Hydrogen Peroxide*," J. Org. Chem. 38:1684-1687; Jensen, H. P. et al. (1975) "*Selenium Dioxide Oxidation Of d-Limonene. Reinvestigation*," J. Org. Chem. 40:264-265) have been investigated, those using TBHP have been reported to form carvone and related compounds derived from hydrogen abstraction at the 6-position, but there has not been prior mention of their optical purity (Lempers, H. E. B. et al. (1996) "*Allylic Oxidation Of Olefins To The Corresponding α,β-Unsaturated Ketones Catalyzed By Chromium Aluminophosphate-5*," Appl. Catal. A: General 143:137-143; Silva, A. D. et al. (2002) "*Wacker PdCl₂—CuCl₂ Catalytic Oxidation Process: Oxidation OfLimonene*," Catal. Commun. 3:435-440).

To determine the eventual fate of reaction products, mixed peroxides 10, 12, and 13 were isolated, purified, and then subjected to reaction conditions similar to those reported for the data of Table 3. The mixed peroxide and dirhodium catalyst were diluted with $CD_2Cl_2$ (to 0.27 M), then treated with 70% TBHP in $D_2O$. Biphenyl was added as an internal standard and the reactions were monitored by $^1H$ NMR. The results of these experiments are described in the following equations, which show that further oxidation occurs, resulting in either ketone formation (9, 11, and 18/eq II) or in the production of a second mixed peroxide (18/eq III, 19, and 20). Perhaps the most remarkable result is that of equation III whereby mixed peroxide 13 is converted, in relatively high yield, to diketone 9, supporting a previously undisclosed catalytic disproportionation pathway for the formation of ketone products via allylic oxidation (Scheme 4). Indeed, this pathway may explain the common inability to detect mixed peroxide products in oxidations by TBHP.

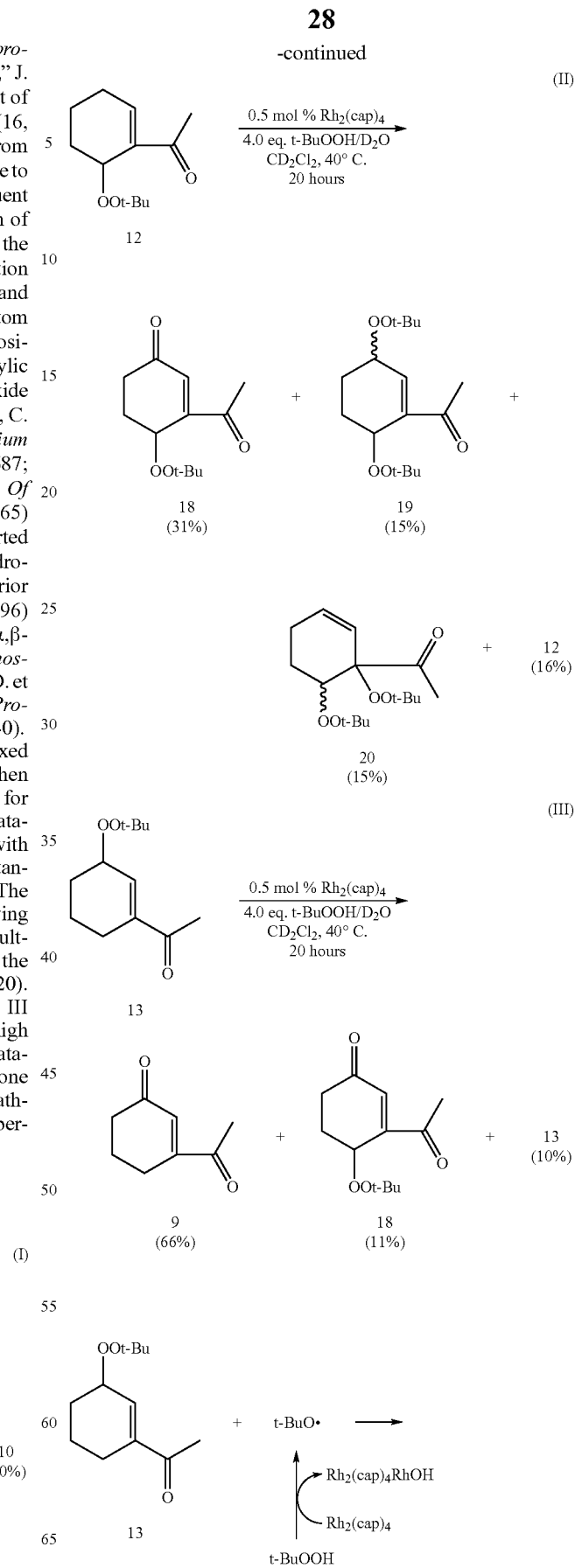

-continued

9 + t-BuOH + t-BuO•

The relative stability of allylic oxidation product 9 is seen in the minor extent of its conversion to mixed peroxide 16 (9→18: 13% yield at 13% conversion after 20 h using the same reaction conditions as in equations I-III). This result is consistent with the low reactivity of α,β-unsaturated carbonyl compounds towards allylic oxidation (see Scheme 1) and to the importance of steric influences in hydrogen atom abstraction reactions of the tert-butylperoxy radical. Interestingly, oxidation of 9 is an order of magnitude less pronounced than oxidation of 1-acetylcyclohexene.

TBHP oxidation of 1-acetylcyclohexene, in association with intermediate allyl radicals 14 and 15 (Scheme 3), presents an opportunity to easily compare the $Rh_2(cap)_4$ catalyzed oxidations with those from other metal catalysts. Oxidation products from reactions of TBHP with 1-acetylcylohexene using several common catalysts using a limited amount of TBHP (4.0 equiv), under exactly the same conditions, are reported in Table 5. Comparison with the anhydrous $Rh_2(cap)_4$ catalytic methodology (Catino, A. J. et al. (2004) "*Dirhodium(II) Caprolactamate: An Exceptional Catalyst for Allylic Oxidation*," J. Am. Chem. Soc. 126: 13622-13623) using TBHP in decane is also provided. Enedione 9, as well as mixed peroxides 10 and 13, are easily identified by their distinctive $^1H$ NMR chemical shifts. Particularly noticeable is the variability in percent conversion (% Conv.), which is a reflection of the turnover rate for production of the active oxidant. Even at 0.1 mol % $Rh_2(cap)_4$ percent conversion is exceptional among the catalysts examined. Of special significance is the low variability in the ratio of 9+13 to 10, which is approximately 1.9±0.3 for all catalysts examined. This value, applicable to all of the catalysts and changing slightly with the amount of catalyst used, suggests that these allylic oxidations occur through the same reaction pathway—via the allyl free radical from hydrogen atom abstraction from the 3-position of 1-acetylcyclohexene—and that the trapping of this intermediate occurs in the same fashion by the same radical species. That the catalyst is not involved in the product forming step is also drawn from the low variability in the ratio of 9+13 to 10, and this conclusion is possibly applicable to prior claims (Shing, T. K. M. et al. (2006) "*Mild Manganese(III) Acetate Catalyzed Allylic Oxidation: Application to Simple and Complex Alkenes*," Org. Lett. 8:3149-3151; Catino, A. J. et al. (2004) "*Dirhodium(II) Caprolactamate: An Exceptional Catalyst for Allylic Oxidation*," J. Am. Chem. Soc. 126:13622-13623; Yu, J.-Q. et al. (2003) "*A Mild, Catalytic, and Highly Selective Method for the Oxidation of α,β-Enones to 1,4-Enediones*, J. Am. Chem. Soc. 125:3232-3233; Bravo, A. et al. (1997) "*Ingold-Fischer "Persistent Radical Effect", Solvent Effect, and Metal Salt Oxidation of Carbon-Centered Radicals in the Synthesis of Mixed Peroxides from tert-Butyl Hydroperoxide*," J. Org. Chem. 62:3849-3857) of metal catalyst involvement in the product determining step in allylic oxidation reactions of TBHP. In addition, intermediate oxo-ruthenium(IV) complexes are often implicated in alkane oxidation reactions catalyzed by ruthenium(III) chloride (Murahashi, S.-I. et al. (2000) "*Ruthenium-Catalyzed Oxidation of Alkanes with tert-Butyl Hydroperoxide and Peracetic Acid*," J. Org. Chem. 65:9186-9193; Lempers, H. E. B. et al. (1998) "*Metal-Catalyzed Oxidations with Pinane Hydroperoxide: A Mechanistic Probe To Distinguish between Oxometal and Peroxometal Pathways*," J. Org. Chem. 63:1408-1413), but the present results suggest that such species are not involved in the allylic oxidation process involving TBHP in water. Also expressed in Table 5, percent conversion of 1-acetylcyclohexene is highest with $Rh_2(cap)_4$, and CuI appears to be only slightly less efficient, but at much higher catalyst loading. Reactions were performed with 1-acetylcyclohexene (0.27 M in $CD_2Cl_2$), using 4.0 equiv 70% TBHP in $D_2O$ and the specified amount of catalyst with 1.0 equiv of biphenyl as internal standard. The reactions were performed in a standard NMR tube, heated to 40° C., and were monitored by $^1H$ NMR. The percent conversion for each reaction was measured by the amount of 1-acetylcyclohexene remaining after 20 hours, relative to the internal standard. The percent yield was determined by the sum of products (9, 10 and 13, as defined above) formed after 20 hours, relative to the internal standard. The results from duplicate runs were reproducible within 5% of the reported values.

TABLE 5

Oxidation of 1-Acetylcyclohexene by TBHP in $CD_2Cl_2$ at 40° C. with Various Catalysts

| Catalyst | Oxidant | % Conv. | % Yield | Relative % Yield 9 | 13 | 10 | Ratio (9 + 13)/10 |
|---|---|---|---|---|---|---|---|
| 0.5 mol % $Rh_2(cap)_4$ | 70% TBHP in water | 80 | 71 | 27 | 34 | 39 | 1.6 |
| 0.1 mol % $Rh_2(cap)$ | 70% TBHP in water | 80 | 63 | 40 | 30 | 30 | 2.3 |
| 0.5 mol % $Rh_2(cap)_4$ 0.5 equiv. $K_2CO_3$ | 6.7 M TBHP in decane | 82 | 49 | 45 | 22 | 33 | 2.0 |
| 2.0 mol % $RuCl_3$•$H_2O$ | 70% TBHP in water | 59 | 42 | 21 | 38 | 40 | 1.5 |
| 2.0 mol % CuI | 70% TBHP in water | 71 | 51 | 24 | 37 | 39 | 1.6 |
| 5.0 mol % $Pd(OH)_2$ | 70% TBHP in water | 38 | 36 | 17 | 50 | 33 | 2.0 |
| 5.0 mol % $Pd(OH)_2$ 0.25 equiv. $K_2CO_3$ | 70% TBHP in water | 62 | 42 | 40 | 31 | 29 | 2.4 |

A mechanistic pathway for Rh$_2$(cap)$_4$-mediated allylic oxidation that is consistent with the reported data is outlined in Scheme 5 using cyclohexene as a model olefinic substrate. Initial oxidation occurs between TBHP and Rh$_2$(cap)$_4$ to form the oxidized dirhodium(II,III) intermediate and the tert-butoxy radical that, in turn, abstracts a hydrogen atom from TBHP at a rate that is much faster than hydrogen atom abstraction from the allylic position of the alkene (Avila, D. V. et al. "*Dramatic Solvent Effects on the Absolute Rate Constants for Abstraction of the Hydroxylic Hydrogen Atom from tert-Butyl Hydroperoxide and Phenol by the Cumyloxyl Radical The Role of Hydrogen Bonding*," (1995) J. Am. Chem. Soc. 117:2929-2930; Bravo, A. et al. (1997) "*Ingold-Fischer "Persistent Radical Effect", Solvent Effect, and Metal Salt Oxidation of Carbon-Centered Radicals in the Synthesis of Mixed Peroxides from tert-Butyl Hydroperoxide*," J. Org. Chem. 62:3849-3857). The tert-butylperoxy radical undergoes selective hydrogen atom abstraction from the hydrocarbon substrate: a process that is well documented and universally accepted (Catino, A. J. et al. (2004) "*Dirhodium(II) Caprolactamate: An Exceptional Catalyst for Allylic Oxidation*," J. Am. Chem. Soc. 126:13622-13623; Choi, H. et al. (2007) "*Optimal TBHP Allylic Oxidation of Δ$^5$-Steroids Catalyzed by Dirhodium Caprolactamate*," Org. Lett. 9:5349-5352; Snelgrove, D. W. et al. (2001) "*Kinetic Solvent Effects on Hydrogen-Atom Abstractions: Reliable, Quantitative Predictions via a Single Empirical Equation*," J. Am. Chem. Soc. 123:469-477; MacFaul, P. A. et al. (1997) "*Oxygen Activation By Metal Complexes And Alkyl Hydroperoxides. Applications Of Mechanistic Probes To Explore The Role Of Alkoxyl Radicals In Alkane Functionalization*," J. Chem. Soc. Perkin Trans. 2:135-145; Chavez, F. A. et al. (2000) "*Co(III)-Alkylperoxo Complexes: Syntheses, Structure-Reactivity Correlations, And Use In The Oxidation Of Hydrocarbons*," Acc. Chem. Res. 33:539-545). The existence of an allylic radical in these reactions is also consistent with the conversion of optically pure limonene into racemic carvone (eq 3). Capture of the allyl radical by the tert-butylperoxy radical (Koola, J. D. et al. (1987) "*Cobalt-Catalyzed Epoxidation Of Olefins. Dual Pathways For Oxygen-Atom Transfer*," J. Org. Chem. 52:4545-4553; Srinavasan, K. et al. (1986) "*Dual Pathways For Manganese Catalysis Of Olefin Oxidation With Alkyl Hydroperoxides*," J. Mol. Catal. 36:297-317) forms the mixed peroxide that is susceptible to tert-butoxy radical catalyzed disproportionation.

Scheme 5

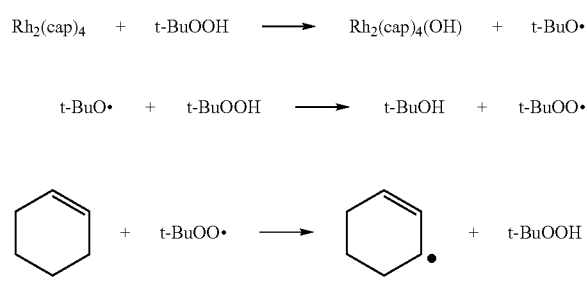

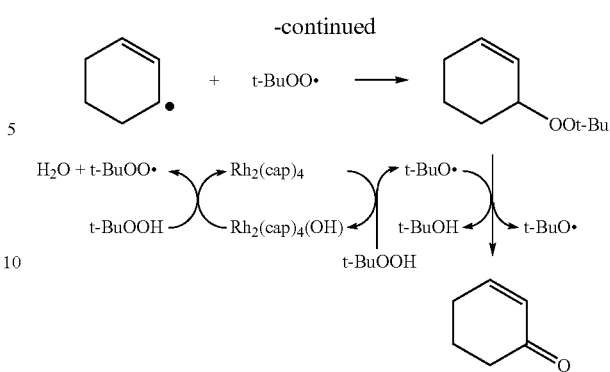

However, mixed peroxides are not observed as reaction intermediates in results from the allylic oxidation of cholesterol 21 to form 7-ketocholesterol 22 and, instead, 7-hydroxycholesterol 23 and the 7-hydroperoxycholesterol 24 in both α and β-stereoisomeric forms are obtained (Choi, H. et al. (2007) "*Optimal TBHP Allylic Oxidation of Δ$^5$-Steroids Catalyzed by Dirhodium Caprolactamate*," Org. Lett. 9:5349-5352; Miller, R. A. et al. (1996) "*A Ruthenium Catalyzed Oxidation Of Steroidal Alkenes To Enones*," Tetrahedron Lett. 37:3429-3432; Nielsen, J. H. et al. (1996) "*Cholesterol Oxidation In A Heterogeneous System Initiated By Water-Soluble Radicals*," Food Chem. 56:33-37). Mixed peroxides analogous to 24 from TBHP oxidation of cholesteryl acetate have been reported as minor products (<5%) (Arsenou, E. S. et al. (2003) "*Optimization Of The Allylic Oxidation In The Synthesis Of 7-Keto-±D5-Steroidal Substrates*," Steroids 68:407-414), and they may be present in lower amounts in related reactions with cholesterol (Miller, R. A. et al. (1996) "*A Ruthenium Catalyzed Oxidation Of Steroidal Alkenes To Enones*," Tetrahedron Lett. 37:3429-3432). Both 23 and 24 are understood to be products of dioxygen capture of an allyl radical in one pathway for the formation of the enone 22 (Miller, R. A. et al. (1996) "*A Ruthenium Catalyzed Oxidation Of Steroidal Alkenes To Enones*," Tetrahedron Lett. 37:3429-3432). Upon close analysis of reaction products from the oxidation of 21, it was possible to identify and isolate α- and β-23 and 24 (eq IV), but we were not able to confirm the presence of mixed peroxides. In addition, based on the seminal work of Schenck (Schenck, G. O. et al. (1958) Justus Liebigs Ann. Chem. 618:202) and similar subsequent reports (Beckwith, A. L. J. et al. (1989) "*The Mechanisms Of The Rearrangements Of Allylic Hydroperoxides: 5-Hydroperoxy-3-Hydroxycholest-6-Ene And 7-Hydroperoxy-3-Hydroxycholest-5-Ene*," J. Chem. Soc. Perkin Trans. 2:815-824; Dang, H. et al. (1990) "*Reactivities Of Some Hydroperoxides Toward Allylic Rearrangement And Related Reactions*," J. Org. Chem. 55:1432-1438; Ponce, M. A. et al. (2000) "*Singlet-Oxygen Ene Reaction With 3β-Substituted Stigmastanes. An Alternative Pathway For The Classical Schenck Rearrangement*," J. Chem. Soc. Perkin Trans. 2:2351-2358) the intermediate allyl radical from hydrogen atom abstraction at the 7-position of cholesterol may form tertiary 5-hydroperoxycholesterol, but this product is not observed due to rapid [2,3]-sigmatropic rearrangement to 7-hydroperoxycholesterol 24.

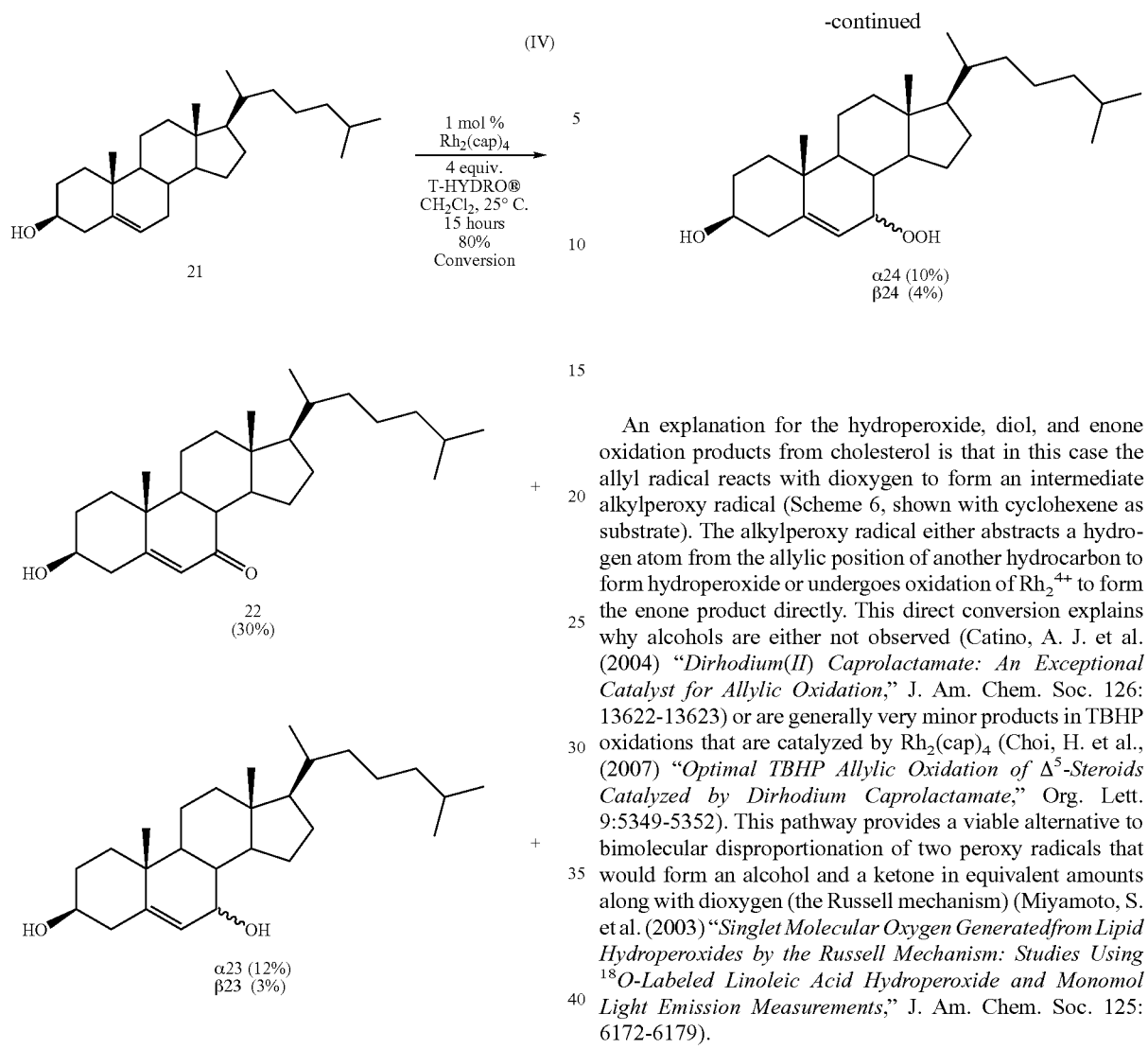

An explanation for the hydroperoxide, diol, and enone oxidation products from cholesterol is that in this case the allyl radical reacts with dioxygen to form an intermediate alkylperoxy radical (Scheme 6, shown with cyclohexene as substrate). The alkylperoxy radical either abstracts a hydrogen atom from the allylic position of another hydrocarbon to form hydroperoxide or undergoes oxidation of $Rh_2^{4+}$ to form the enone product directly. This direct conversion explains why alcohols are either not observed (Catino, A. J. et al. (2004) "*Dirhodium(II) Caprolactamate: An Exceptional Catalyst for Allylic Oxidation*," J. Am. Chem. Soc. 126: 13622-13623) or are generally very minor products in TBHP oxidations that are catalyzed by $Rh_2(cap)_4$ (Choi, H. et al., (2007) "*Optimal TBHP Allylic Oxidation of $\Delta^5$-Steroids Catalyzed by Dirhodium Caprolactamate*," Org. Lett. 9:5349-5352). This pathway provides a viable alternative to bimolecular disproportionation of two peroxy radicals that would form an alcohol and a ketone in equivalent amounts along with dioxygen (the Russell mechanism) (Miyamoto, S. et al. (2003) "*Singlet Molecular Oxygen Generated from Lipid Hydroperoxides by the Russell Mechanism: Studies Using $^{18}O$-Labeled Linoleic Acid Hydroperoxide and Monomol Light Emission Measurements*," J. Am. Chem. Soc. 125: 6172-6179).

Scheme 6

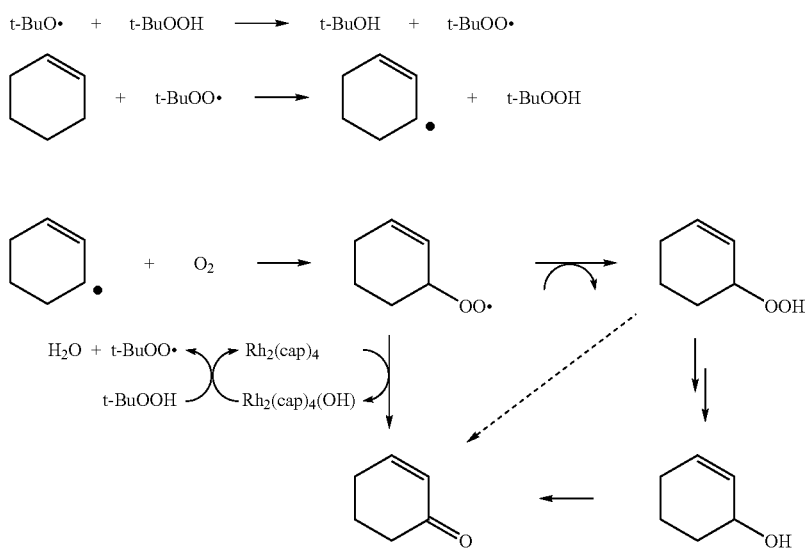

The oxidations of testosterone (eq V), 17-acetyltestosterone (eq VI), 4-androstene-3,17-dione (eq VII), and 4-cholesten-3-one (eq VIII) were performed under the same conditions as those reported for the reactions of Table 3. Although using 1,2-dichloroethane as solvent was initially believed to be necessary to dissolve the water-insoluble steroidal compounds, examination of the oxidation process using water as solvent actually led to an improvement in product yield (e.g., 68% yield for 29 after 48 h with 12 equiv of T-HYDRO®). In contrast to oxidations of cholesterol in which the secondary alcohol at the 3-position was stable to oxidative conversion to a ketone, oxidation of the secondary alcohol at the 17-position of testosterone was competitive with allylic oxidation of the enone, and both androst-4-ene-3,17-dione and androst-4-ene-3,6,17-trione accompanied formation of 25. This oxidative process appears to be general for strained secondary alcohols (cyclopentanol, endo-norbornanol, borneol, for example). In an attempt to effect sequential oxidation on both sides of the carbon-carbon double bond, 3β-acetoxyandrost-5-en-17-one was subjected to sequential treatments with TBHP and $Rh_2(cap)_4$ (eq IX); the desired 3β-acetoxyandrost-5-en-4,7,17-trione 29 was formed in 54% yield.

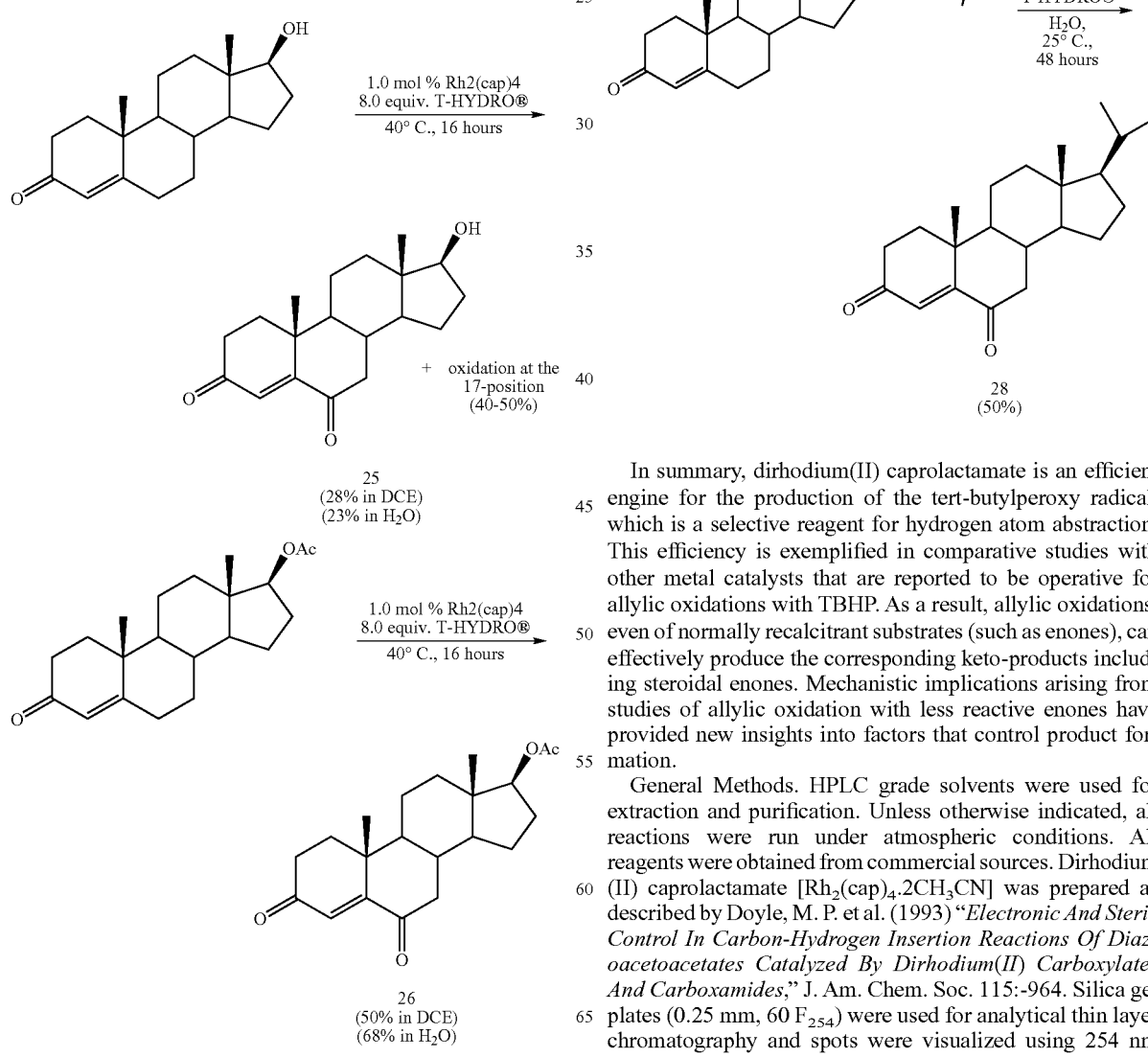

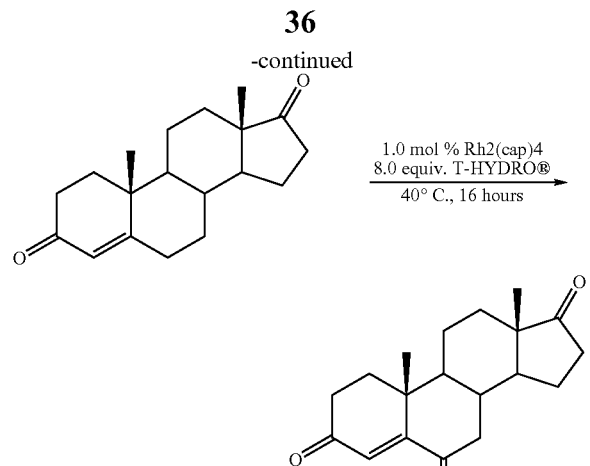

In summary, dirhodium(II) caprolactamate is an efficient engine for the production of the tert-butylperoxy radical, which is a selective reagent for hydrogen atom abstraction. This efficiency is exemplified in comparative studies with other metal catalysts that are reported to be operative for allylic oxidations with TBHP. As a result, allylic oxidations, even of normally recalcitrant substrates (such as enones), can effectively produce the corresponding keto-products including steroidal enones. Mechanistic implications arising from studies of allylic oxidation with less reactive enones have provided new insights into factors that control product formation.

General Methods. HPLC grade solvents were used for extraction and purification. Unless otherwise indicated, all reactions were run under atmospheric conditions. All reagents were obtained from commercial sources. Dirhodium (II) caprolactamate [$Rh_2(cap)_4 \cdot 2CH_3CN$] was prepared as described by Doyle, M. P. et al. (1993) "*Electronic And Steric Control In Carbon-Hydrogen Insertion Reactions Of Diazoacetoacetates Catalyzed By Dirhodium(II) Carboxylates And Carboxamides*," J. Am. Chem. Soc. 115:-964. Silica gel plates (0.25 mm, 60 $F_{254}$) were used for analytical thin layer chromatography and spots were visualized using 254 nm ultraviolet light before using potassium permanganate, vanillin, or anisaldehyde stains as visualizing agents. Chromatographic purifications were performed using silica gel (60 microns, 40-63 mesh) according to the method of Still (Doyle, M. P. et al. (1993) "*Electronic And Steric Control In Carbon-Hydrogen Insertion Reactions Of Diazoacetoacetates Catalyzed By Dirhodium(II) Carboxylates And Carboxamides*," J. Am. Chem. Soc. 115:958-964). Yields reported are for isolated compounds according to their mass unless otherwise noted. All products were characterized and in agreement with those that were previously described. $^1$H NMR (400 MHz) and $^{13}$C NMR (100 MHz) spectra were obtained on a 400 MHz spectrometer as solutions in CDCl$_3$ unless otherwise noted. Chemical shifts are reported in parts per million (ppm, δ) relative to internal Me$_4$Si (δ 0.00) for $^1$H and relative to internal chloroform (δ 77.0) for $^{13}$C; coupling constants are reported in Hertz (Hz).

General Procedure for the Oxidation of α,β-Unsaturated Carbonyl Compounds. A 10 mL vial equipped with a stirbar was charged with substrate (1.36 mmol) and Rh$_2$(cap)$_4$ (5 mg, 0.007 mmol). Solvent (2.5 mL) was added followed by the addition of TBHP (0.75 mL, 5.5 mmol, 4 equiv). The vial was loosely capped and stirred for 16 hrs, then the second portion of Rh$_2$(cap)$_4$ (5 mg, 0.007 mmol) and TBHP (0.75 mL, 5.5 mmol, 4 equiv) was added. After an additional 24 hrs, the solution was concentrated and purified by column chromatography to obtain analytically pure compounds whose spectral characteristics were identical to those previously reported: trans-3-nonen-2,5-dione (1) (Yu, J.-Q. et al. (2003) "*A Mild, Catalytic, and Highly Selective Method for the Oxidation of α,β-Enones to 1,4-Enediones*, J. Am. Chem. Soc. 125:3232-3233) ethyl (E)-4-oxo-2-decenoate (2) (Manfredini, S. et al. (1988) "*A Convenient Synthesis Of λ-Oxo-Acrylates*," Tetrahedron Lett. 29:3997-4000), (E)-4-oxo-2-pentenamide (5) (Scheffold, R. et al. (1967) "*Synthese Von Azaprotoanemoninen*," Helv. Chim. Acta. 50:798-808), 4-androsten-17-3,6-dione (28) (Jasiczak, J. (1988) "*Oxidations Of Enone Systems In Steroids By Oxidizers With Reversible Redox Potential*," J. Chem. Soc. Perkin Trans. 1, 10, 2687-2692), 17β-acetoxyandrost-4-en-3,6-dione (29) (Marwah, P. et al. (2004) "*An Economical And Green Approach For The Oxidation Of Olefins To Enones*," Green Chem. 570-577), 4-androstene-3,6,17-trione (30) (Kiran, I. J. (2004) "*An Alternative Preparation Of Steroidal Δ4-3,6-Diones*," Chem. Res. 3:208-209), 4-cholesten-3,6-dione (31) (Hunter, C. A. et al. (2006) "*An Efficient One-Pot Synthesis Generating 4-Ene-3, 6-Dione Functionalised Steroids From Steroidal 5-En-3β-ols Using A Modified Jones Oxidation Methodology*," Steroids 71:30-33) and acids were purified by recrystallization in ethyl acetate and matched with those in the literature: (E)-4-oxo-2-nonenoic acid (3) (Ballini, R. et al. (1998) "*Synthesis of (E)-4-Oxonon-2-enoic Acid, a Natural Antibiotic Produced by Streptomyces olivaceus*," J. Nat. Prod. 61:673-674), (E)-4-oxo-2-pentenoic acid (4) (Lüüond, R. M. et al. (1992) "*Assessment Of The Active-Site Requirements Of 5-Aminolevulinic Acid Dehydratase: Evaluation Of Substrate And Product Analogs As Competitive Inhibitors*," J. Org. Chem. 57:5005-5013), 2-cyclohexenone-1-carboxylic acid (7) (Webster, F. X. et al. (1987) "*Control Of The Birch Reduction Of m-Anisic Acid To Produce Specific 3-Oxocyclohexenecarboxylic Acids*," Synthesis 10:922-923) and fumaric acid monomethyl ester (8) (Davis, R. A. (2005) "*Isolation and Structure Elucidation of the New Fungal Metabolite (−)-Xylariamide A*," J. Nat. Prod. 68:769-772).

Oxidation of 1-Acetylcyclohexene—Isolation and Characterization of 10, 11, 12, 13 and 18. 1-Acetylcyclohexene (0.750 g; 6.04 mmol) and Rh$_2$(cap)$_4$ (22 mg; 0.030 mmol) were dissolved in 22 mL of 1,2-dichloroethane in a 100 mL round-bottom flask. T-HYDRO® (3.31 mL; 24.1 mmol) was slowly added (1 mL/minute), and the color of the reaction solution turned from purple to brown-red in color. The flask was capped with a rubber septum, vented with a 18-gauge needle, and heated at 40° C. in an oil bath. After 17.5 hours, the reaction was concentrated under reduced pressure to yield 2.11 g of a red-brown oil. The oil was purified via silica gel column chromatography (100% hexanes to 2:1 hexanes: ethyl acetate, gradient). Only the purest fractions were used for full characterization: 55 mg of 10, 20 mg of 11, 18 mg of 12, 32 mg of 13, 20 mg of 16, and 312 mg of 3-acetyl-2-cyclohexenone (9).

1-(1-tert-Butylperoxy)cyclohex-2-enyl)ethanoate (10). Rf 0.69 (20% EtOAc/hexanes); $^1$H NMR (400 MHz, CDCl$_3$) δ 6.12 (ddd, J=3.2, 4.4, 10.0 Hz, 1H), 5.66 (ddd, J=2.0, 2.0, 10.0 Hz, 1H), 2.31 (s, 3H), 2.07-2.02 (comp, 2H), 1.97-1.91 (comp, 2 H), 1.73-1.65 (comp, 2H), 1.23 (s, 9H); $^{13}$C NMR (100 MHz, CDCl$_3$) δ 210.0, 135.6, 123.0, 85.2, 79.7, 26.9, 26.6, 25.3, 24.4, 18.2; FTIR (thin film) 2979, 2935, 2871, 1720, 1363, 1197, 735 cm$^{-1}$. Exact mass calculated for C$_{12}$H$_{20}$O$_3$+H (ES) 213.1490. Found 213.1115.

4-(tert-Butylperoxy)-4-ethanoylcyclohex-2-enone (11). Rf 0.37 (20% EtOAc/hexanes); $^1$H NMR (400 MHz, CDCl$_3$) δ6.99 (d, J=10.4 Hz, 1H), 6.17 (d, J=10.4 Hz, 1H), 2.57 (m, 1H) 2.46-2.44 (comp, 2H), 2.38 (s, 3H), 2.27-2.22 (comp, 3H), 1.25 (s, 9H); $^{13}$C NMR (100 MHz, CDCl$_3$) δ 207.6, 198.0, 145.2, 131.8, 84.4, 81.06, 33.3, 28.7, 26.4, 24.6; FTIR (thin film) 3056, 2980, 2937, 1720, 1688, 1365, 1192, 874, 737 cm$^{-1}$. Exact mass calculated for C$_{12}$H$_{18}$O$_4$+H (ES) 227.1283. Found 227.1288.

1-(6-tert-Butylperoxy)cyclohex-1-enyl)ethanoate (12). Rf 0.58 (20% EtOAc/hexanes); $^1$H NMR (400 MHz, CDCl$_3$) δ 7.08 (dd, J=4.8, 2.8 Hz, 1H), 5.00 (bs, 1 H), 2.40-2.38 (comp, 2H), 2.35 (m, 1H), 2.32 (s, 3H), 2.20-2.17 (m, 1H), 1.75-1.78 (m, 1 H), 1.63-1.66 (m, 1H), 1.26 (s, 9H); $^{13}$C NMR (100 MHz, CDCl$_3$) δ 198.0, 146.1, 136.2, 80.1, 72.1, 26.5, 26.3, 26.0, 25.4, 15.7; FTIR (thin film) 3060, 2928, 2977, 1674, 1362, 1258, 1240, 1196, 736 cm$^{-1}$. Exact mass calculated for C$_{12}$H$_{20}$O$_3$+H (ES) 213.1490. Found 213.1481.

1-(3-tert-Butylperoxy)cyclohex-1-enyl)ethanoate (13). Rf 0.62 (20% EtOAc/hexanes); $^1$H NMR (400 MHz, CDCl$_3$) δ 6.86 (t, J=1.5 Hz, 1H), 4.63 (bs, 1H), 2.34 (s, 3H), 2.25-2.19 (comp, 2H), 1.87-1.70 (comp, 3H), 1.63-1.61 (m, 1H), 1.28 (s, 9H); $^{13}$C NMR (100 MHz, CDCl$_3$) d 199.7, 142.3, 136.3, 80.4, 77.4, 26.4, 26.3, 25.6, 23.3, 18.9; FTIR (thin film) 3055, 2980, 2930, 1672, 1265, 1235, 734 cm$^{-1}$. Exact mass calculated for C$_{12}$H$_{20}$O$_3$ (CI) 214.1412. Found 214.1481.

4-(tert-Butylperoxy)-3-ethanoylcyclohex-2-enone (18). Rf 0.33 (20% EtOAc/hexanes); $^1$H NMR (400 MHz, CDCl$_3$) δ 6.53 (s, 1H), 5.16 (t, J=3.2 Hz, 1H), 2.81 (ddd, J=5.2, 12.8, 17.6 Hz, 1H), 2.62-2.60 (m, 1H), 2.47-2.45 (m, 1H), 2.44 (s, 3H), 200 (m, 1H), 1.23 (s, 9H); $^{13}$C NMR (100 MHz, CDCl$_3$) δ 200.7, 198.9, 149.4, 133.6, 81.0, 71.41, 32.9, 26.8, 26.3, 25.7; FTIR (thin film) 2982, 2937, 2253, 1685, 1365, 1222, 1191, 907, 736 cm$^{-1}$. Exact mass calculated for C$_{12}$H$_{18}$O$_4$+H (ES) 227.1283. Found 227.1259.

Oxidation of Cholesterol (19)—Isolation of 22, 23, and 24. Cholesterol (0.525 g; 1.36 mmol) and Rh$_2$(cap)$_4$ (10 mg; 0.013 mmol) were dissolved in 5 mL of 1,2-dichloroethane in a 6 dram vial equipped with a stirbar. T-HYDRO® (0.74 mL; 5.43 mmol) was added, and the color of the reaction solution turned from purple to brown-red in color. The vial was loosely capped and stirred at room temperature. After 15 hours, the reaction was concentrated under reduced pressure to 1.01 g of a red-brown semi-solid. The crude material was purified via silica gel column chromatography (100% hexanes to 1:1 hexanes: ethyl acetate, gradient) to afford 164 mg of 22, 62 mg of α-23, 13 mg of β-23, 57 mg of α-24, 25 mg of β-24, and 106 mg of starting material (21). The full characterization of 22, 23, and 24 has been reported (Choi, H. et al. (2007) "*Optimal TBHP Allylic Oxidation of $\Delta^5$-Steroids Catalyzed by Dirhodium Caprolactamate*," Org. Lett. 9:5349-5352; Beckwith, A. L. J. et al. (1989) "*The Mechanisms Of The Rearrangements Of Allylic Hydroperoxides: 5-Hydroperoxy-3-Hydroxycholest-6-Ene And 7-Hydroperoxy-3-Hydroxycholest-5-Ene*," J. Chem. Soc. Perkin Trans. 2:815-824).

Oxidation of 17β-Acetoxyandrost-4-en-3-one in Water. 17β-Acetoxyandrost-4-en-3-one (17β-Acetoxyandrost-4-en-3-one was prepared according to Krauser, J. A. et al. (2005) "*Cytochrome P450 3a4-Catalyzed Testosterone 6-Hydroxylation Stereochemistry, Kinetic Deuterium Isotope Effects, And Rate-Limiting Steps*," J. Biol. Chem. 280:19496-19506) (1.32 g, 4.0 mmol) was stirred vigorously in 12 mL of water at room temperature in a 50 mL flask. Then $Rh_2(cap)_4$ (29.5 mg, 0.040 mmol) was added, followed by addition of T-HYDRO® (4.6 mL; 32 mmol). The reaction became dark purple-red in color. The flask was closed with a rubber septum with a balloon and stirred for 24 h in a 40° C. oil bath. At that time additional portions of $Rh_2(cap)_4$ (15 mg, 0.02 mmol) and T-HYDRO® (2.3 mL; 16 mmol) were added, and the reaction solution was stirred for another 24 h. The reaction was extracted into diethyl ether (3×20 mL). The organic extracts were combined, dried over anhydrous $MgSO_4$, filtered, then concentrated under reduced pressure to yield a crude yellow oil that was purified by silica gel chromatography (25% ethyl acetate in hexanes) to yield 938 mg (2.72 mmol, 68%) of a white solid (29) m.p. 193-195° C.; 192-194° C. (lit.) (Marwah, P. et al. (2004) "*An Economical And Green Approach For The Oxidation Of Olefins To Enones*," Green Chem. 570-577).

3β-Acetoxyandrost-5-en-4,7,17-trione (30). 3β-Acetoxyandrost-5-en-17-one (330 mg, 1.0 mmol) and $Rh_2(cap)_4$ (7.4 mg, 10 μmol) were added into a vial together with 3 mL of water was added, followed by T-HYDRO® (1.14 mL, 8.0 mmol), and the stirred reaction mixture was heated in an oil bath at 40° C. After 24 h and 48 h, additional portions of $Rh_2(cap)_4$ (7.4 mg, 10 μmol) and T-HYDRO® (1. 14 mL, 8.0 mmol) were added. The reaction was extracted into diethyl ether (3×20 mL), the organic extracts were combined, dried over anhydrous $MgSO_4$, filtered, then concentrated, under reduced pressure, to yield a crude yellow oil that was purified by silica gel chromatography (33% ethyl acetate in hexanes) to give 195 mg (0.54 mmol, 54%) of a white solid: m.p. 216-218° C.; 218-220° (lit.) (Marwah, P. et al. (2004) "*An Economical And Green Approach For The Oxidation Of Olefins To Enones*," Green Chem. 570-577). $^1$H NMR ($CDCl_3$, 400 MHz): defining absorptions are at δ 6.15 (s, 1H), 5.28 (dd, J=12.0, 8.0 Hz, 1H), 2.77 (ddd, J=12.0, 8.0, 4.0 Hz, 1H), 2.50 (d, J=8.0 Hz, 1H), 2.45 (d, J=8.0 Hz, 1H), 2.24-2.31 (m, 1H), 2.18 (s, 3H), 1.22 (s, 3H), 0.90 (s, 3H).

Example 3

Optimization of Aqueous Allylic Oxidation Conditions of Steroidal Compounds

In order to determine aqueous allylic oxidation reaction conditions for the synthesis of 7-keto steroids, reaction parameters (temperature, TBHP concentration, co-solvent, base and reaction time) were varied and their effect on reaction yield was determined for the reaction:

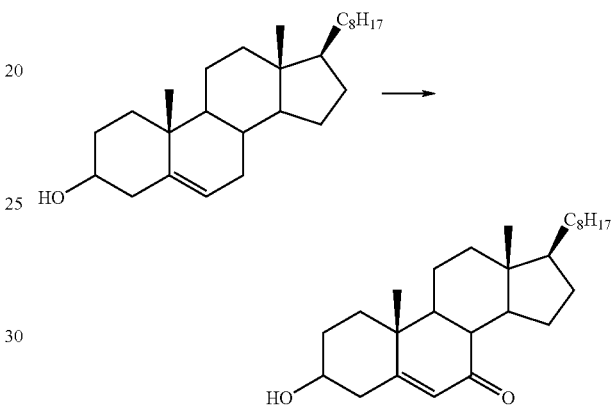

In all cases, the reaction was conducted using 1 mol % $Rh_2(cap)_4$, T-HYDRO® (TBHP 70% aqueous solution; Aldrich) and specified solvent (DCM=dichloromethane; DCE=dichloroethane) as indicated in Table 6. The reactions were conducted under conditions of temperature (RT=room temperature (22-25° C.)) as indicated in Table 6.

TABLE 6

| Entry | $Rh_2(cap)_4$ | ° C. | T-HYDRO ® | Base | Co-Solvent | Time | Yield |
|---|---|---|---|---|---|---|---|
| 1 | 1 mol % | RT | 4 Equiv.; dropwise | — | DCM | | 53 |
| 2 | 1 mol % | RT | 6 Equiv. | — | DCM | 20 h | 68 |
| 3 | 1 mol % | RT | 8 Equiv. | — | DCM | 20 h | 72 |
| 4 | 1 mol % | 40° C. | 1.5 Equiv. | — | DCE | 20 h | 38 |
| 5 | 1 mol % | 40° C. | 2 Equiv. | — | DCE | 20 h | 64 |
| 6 | 1 mol % | 40° C. | 4 Equiv. | — | DCE | 20 h | 64 |
| 7 | 1 mol % | 40° C. | 4 Equiv. | $K_2CO_3$ | DCE | 20 h | LC |
| 8 | 1 mol % | 40° C. | 5 Equiv. | — | DCE | 20 h | 63* |
| 9 | 1 mol % | 60° C. | 2 Equiv. | — | DCE | 8 h | 53 |
| 10 | 1 mol % | 60° C. | 4 Equiv. | — | DCE | | 40 |

*less alcohol formation;
LC = low conversion

The reaction conditions of Entry 8 of Table 6 (shaded) were considered to be the optimized conditions.

Example 4

Diversity of Substrates Amenable to Aqueous Allylic Oxidation

Reactions were conducted with several 7-keto steroid substrates and other compounds under the conditions of Entries 6 or 8 of Table 6, and the yield of product was measured (Table 7).

General. All products were characterized and in agreement with those previously described. Yields reported are for isolated yields unless otherwise noted. tert-Butyl hydroperoxide (T-HYDRO® (Aldrich), 70 wt. % in $H_2O$) was obtained from Aldrich and used as received. Dirhodium(II) caprolactamate [$Rh_2(cap)_4 \cdot CH_3CN$] was prepared as described by Doyle, M. P. et al. (1993) *"Electronic And Steric Control In Carbon-Hydrogen Insertion Reactions Of Diazoacetoacetates Catalyzed By Dirhodium(II) Carboxylates And Carboxamides,"* J. Am. Chem. Soc. 115:958-964). Preparative chromatographic purification was performed using SiliCycle (60 Å, 40-63 mesh) silica gel according to the method of Still (Still, W. C. et al. (1978) *"Rapid Chromatographic Technique For Preparative Separations With Moderate Resolution,"* J. Org. Chem. 43:2923-2925). Thin layer chromatography (TLC) was performed on Merck 0.25 mm silica gel 60 $F_{254}$ plates with visualization by fluorescence quenching. $^1H$ NMR (400 MHz) and $^{13}C$ NMR (100 MHz) spectra were obtained on a Bruker DRX-400 NMR as solutions in $CDCl_3$. Chemical shifts are reported in parts per million (ppm), δ downfield from $Me_4Si$ (TMS); coupling constants are reported in Hertz (Hz).

Representative Procedure. A 10 mL round-bottomed flask equipped with a stirbar was charged with substrate (0.81 nmols) and $Rh_2(cap)_4$ (0.0081 mmols). Solvent ($H_2O$ or 1,2-dichloroethane; 3 mL) was added followed by the addition of TBHP (4.07 mmols, 5 equiv) vi8a syringe. The flask was sealed, vented and heated to temperature. The reaction mixture was stirred for 20 hrs and monitored by TLC. For aqueous reactions, the organic material was extracted with ethyl acetate (30 mL), concentrated and purified via column chromatography (hexane/ethylacetate), but this is not essential. Reactions performed in 1,2-dichloroethane were concentrated and purified by column chromatography, but this is not essential. Table 7 shows the substrates, product and yield.

TABLE 7

| Entry | Substrate | Product | % Yield |
|---|---|---|---|
| 1 | | | 65[a,b] |
| 2 | | | 64[a,c]<br>60[a,d] |
| 3 | | | 60[a,c]<br>52[a,d]<br>60[f] |
| 4 | | | 63[a,d]<br>63[e]<br>58[e] |
| 5 | | | 80[a,d]<br>80[e] |
| 5 | | | 73[a,d]<br>73[e] |

TABLE 7-continued

| Entry | Substrate | Product | % Yield |
|---|---|---|---|
| 7 | (steroid with AcO and C=C, ketone) | (steroid with AcO, C=C, ketone, and added =O) | 87[a,d] 87[e] |
| 8 | (4-methyl-1-(prop-1-en-2-yl)cyclohexane) | (2-methyl-5-(prop-1-en-2-yl)cyclohexan-1-one) | 42[f] |
| 9 | CH₃-CH=CH-CO₂H | CH₃-C(O)-CH=CH-CO₂H | 70[a,d] |
| 10 | (citronellol) | (hydroperoxide product with OH) | g |

Table Notes:
[a] Reactions were performed at 40° C. for 20 hours using $Rh_2(cap)_4$ (1.0 mol %), substrate (1.0 equivalents), and TBHP (70% aqueous solution, 4.0 equivalents). All yields are reported as isolated yields
[b] 5% ethanol in water as solvent (0.27 M/[substrate])
[c] water as solvent (0.27 M/[substrate])
[d] 1,2, dichloroethane as solvent (0.27 M/[substrate])
[e] Reactions were performed at 40° C. for 20 hours using $Rh_2(cap)_4$ (1.0 mol %), substrate (1.0 equivalents), and TBHP (70% aqueous solution, 5.0 equivalents). All yields are reported as isolated yields
[f] Reactions were performed at room temperature using $Rh_2(cap)_4$ (1.0 mol %), substrate (1.0 equivalents), and TBHP (70% aqueous solution, 4.0 equivalents). All yields are reported as isolated yields
[g] Trapping by dioxygen As further evidence of the expanded range of substrates amenable to the aqueous allylic oxidation of the present invention, oxidation of butylbenzene was attempted under aqueous conditions (1.0 mol % $Rh_2(cap)_4$, T-HYDRO®/$H_2O$, 40° C.) or anhydrous conditions (1.0 mol % $Rh_2(cap)_4$, t-BuOOH/decane, DCE, 40° C.). Product (1-phenybutan-1-one)) was recovered under the aqueous reaction conditions, but was not obtained under anhydrous synthesis conditions.

The Example shows that dirhodium(II,II) caprolactamate used in conjunction with aqueous TBHP (T-HYDRO®) in the presence or absence of a co-solvent is an efficient, mild and selective oxidant for hydrocarbon oxidations, and in particular, for the allylic oxidation of steroids and complex organic compounds. The results indicate that TBHP is a more active oxidant in water than in organic solvents.

Example 5

Extension of Allylic Oxidation to Enamides and Enol Ethers

The mild conditions of the optimized aqueous $Rh_2(cap)_4$/tert-Butyl hydroperoxide oxidation reaction of the present invention provides a means for extending allylic oxidation to enamides and enol ethers.

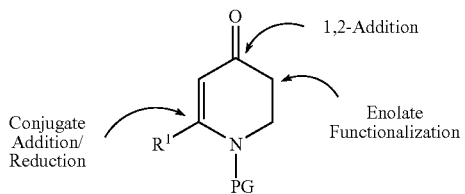

Reactions were conducted in the presence of $Rh_2(cap)_4$ (0.1 mol %); K2CO3 and t-BuOOH (Table 8).

TABLE 8

| Entry | Substrate | Product | % Yield |
|---|---|---|---|
| 1 | (N-Cbz tetrahydropyridine with CH₃) | (N-Cbz dihydropyridinone with CH₃) | 73 |

TABLE 8-continued

| Entry | Substrate | Product | % Yield |
|---|---|---|---|
| 2 | (piperidine N-Boc, ring with double bond, n=1 or 2) | (piperidinone N-Boc, n=1 or 2) | 66 (n = 1)<br>41 (n = 2) |
| 3 | OSi(i-Pr)₃ cyclohexenyl silyl ether | OSi(i-Pr)₃ cyclohexenone silyl ether | 81 |
| 4 | 2,3-dihydrofuran | γ-butyrolactone (furan-2(5H)-one) | 62 |

Example 6

Extension of Benzylic Oxidation

The mild conditions of the optimized aqueous Rh$_2$(cap)$_4$/tert-Butyl hydroperoxide allylic oxidation reaction of the present invention provides an improved means for conducting benzylic oxidation and dione formation. Anhydrous benzylic reactions are discussed in Catino, A. J. et al. (2005) Org. Lett., 7(23):5167-5170), and involve Rh$_2$(cap)$_4$ (1.0 mol %); NaHCO3 (50 mol %), t-BuOOH (5.0 equiv.), DCE, room temperature, 16 hour incubation) (Table 9).

TABLE 9

| Entry | Substrate | Product | % Yield |
|---|---|---|---|
| 1 | α-tetralone | 1,4-dihydronaphthalene-1,4-dione derivative | 27 |
| 2 | 6-methoxy-α-tetralone | 6-methoxy-naphthalene-1,4-dione | 33 |

A survey of suitable substrates for benzylic oxidation reactions includes the following compounds (see, Catino, A. J. et al. (2005) Org. Lett., 7(23):5167-5170). Reactions were conducted using Rh$_2$(cap)$_4$ (1.0 mol %); NaHCO3 (50 mol %), t-BuOOH (5.0 equiv.), DCE, room temperature, 16 hour incubation) (Table 10).

General Procedure for Benzylic Oxidations Catalyzed by Dirhodium(II) Caprolactamate in Water. 1-Phenylbutane was stirred vigorously in water at room temperature in a screwcap vial. Rh$_2$(cap)$_4$ (1.0 mol %) was added to the vial followed by dropwise (2 drops/sec) addition of 5.0 equiv. of T-HYDRO®. The reaction was slightly exothermic, bubbled, and the mixture became dark purple-red in color. The vial was loosely capped and stirred at room temperature or heated to 40° C. while monitored by TLC and gas chromatography. Upon consumption of the starting arylhydrocarbon, the reaction was extracted twice into diethyl ether. The organic extracts were combined, dried over anhydrous MgSO$_4$, filtered, then concentrated on a under reduced pressure to a crude oil which was purified via silica gel chromatography (hexanes/ethyl acetate) to afford the desired product. Benzylic oxidations run under aqueous conditions are reported in McLaughlin, E. C.; Doyle, M. P. *J. Org. Chem.* 2008, 73, 4317

TABLE 10

| Entry | Substrate | Product | % Yield |
|---|---|---|---|
| 1 | 1-phenylbutane | 1-phenylbutan-1-one | 92 |

Example 7

Oxidation of Secondary Amines

Rh$_2$(cap)$_4$/tert-Butyl hydroperoxide can be used under anhydrous conditions to mediate the oxidation of secondary amine, as shown below:

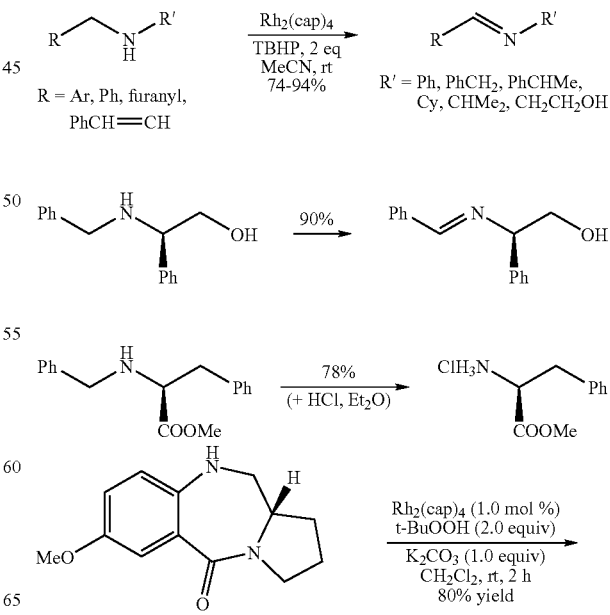

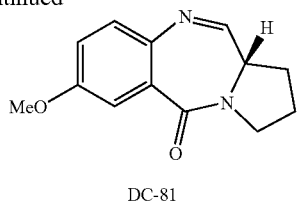

DC-81

N-Phenylbenzylamine (1) was selected to determine suitable conditions for oxidation with TBHP catalyzed by $Rh_2(cap)_4$ at 1.0 mol % catalyst loading (Table 1). Previously described conditions for benzylic oxidation (entry 1)[9b] gave complete conversion of 1, but benzylidineaniline (2) was accompanied by its hydrolysis product benzaldehyde (3). Benzaldehyde formation with complete substrate conversion was diminished in the absence of $NaHCO_3$ (entry 2). Attempts to decrease the extent of hydrolysis even further using molecular sieves or anhydrous $MgSO_4$ were unsuccessful (entries 3 and 4) because they significantly limited the oxidation of 1. Methanol, the solvent of choice for the oxidation of N-aryl tertiary amines,[10] was found be effective (entry 5); however, when N-cyclohexylbenzylamine was submitted to reaction under the same conditions, no imine product was obtained at room temperature (entry 6), and only trace amounts were obtained at temperatures up to 60° C. However, the use of acetonitrile as the solvent gave optimal results for both N-phenyl- and N-cyclohexylbenzylamine substrates (entries 7 and 8) with quantitative conversion, chromatographically pure product in high yield, and the absence of hydrolysis. We assume that steric effects in the two solvents are responsible for the difference in reaction outcomes (entries 6 and 8).

TABLE 11

Optimization of the Conditions for the Oxidation of Benzylphenylamine[a]

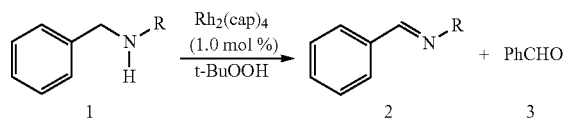

| Entry | R  | Conditions                                          | Conv %      | Ratio 2:3[b] |
|-------|----|-----------------------------------------------------|-------------|--------------|
| 1     | Ph | $CH_2Cl_2$, $NaHCO_3$ (50 mol %)                    | >95         | 48:52        |
| 2     | Ph | $CH_2Cl_2$                                          | >95         | 80:20        |
| 3     | Ph | $CH_2Cl_2$, 4Å MS (50 wt %)                         | 28          | 90:10        |
| 4     | Ph | $CH_2Cl_2$, $MgSO_4$ (1 equiv)                      | 56          | 90:10        |
| 5     | Ph | MeOH                                                | >95         | >95:5        |
| 6     | Cy | MeOH                                                | 0           | —            |
| 7     | Ph | $CH_3CN$                                            | >95 (94)[c] | >95:5        |
| 8     | Cy | $CH_3CN$                                            | >95 (90)[c] | >95:5        |

Table Notes:
[a] Reactions were performed using $Rh_2(cap)_4$ (1.0 mol %), amine (1.0 equiv), t-BuOOH (6.5 M in decane, 2.0 equiv), and solvent at room temperature for 16 hours.
[b] Determined by $^1H$ NMR.
[c] Isolated yield of analytically pure compound

Example 8

Oxidation of Tertiary Amines

The mild conditions of the optimized aqueous $Rh_2(cap)_4$/ tert-Butyl hydroperoxide oxidation reaction of the present invention also provide a means for conducting the oxidation of tertiary amines through an iminium ion intermediate, as shown below.

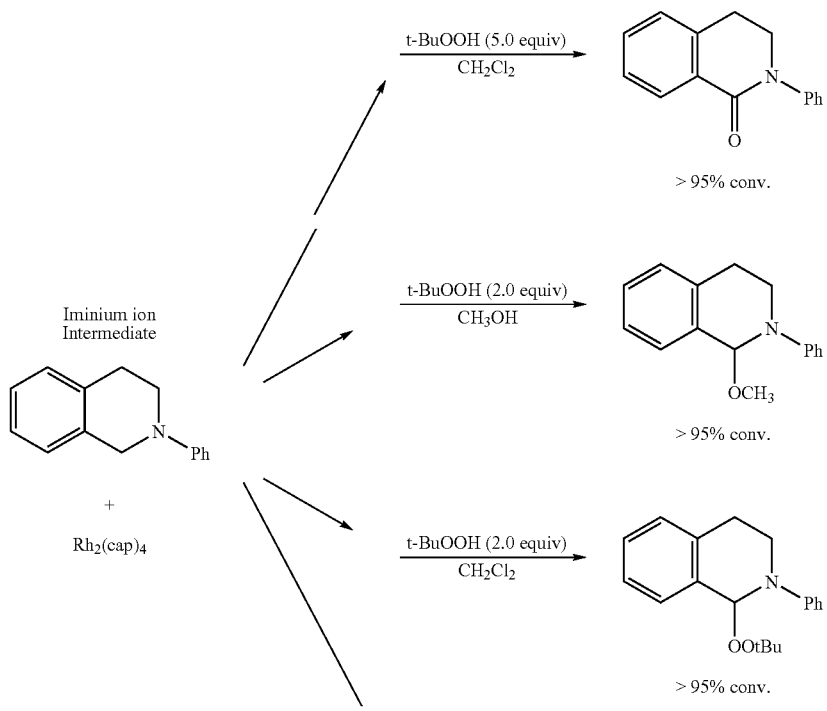

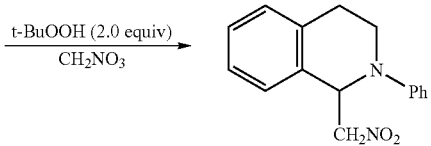

> 95% conv.

General Procedure for the Oxidative Mannich Reaction Catalyzed by Rh$_2$(cap)$_4$. T-HYDRO® (1.2 equiv) was added in one portion to a stirring solution of amine (2.0 equiv), 2-triisopropoxysilylfuran (1.0 equiv), and Rh$_2$(cap)$_4$ (1.0 mol %) in MeOH (0.27 M/[siloxyfuran]). The reaction mixture was heated at 60° C. for 3-5 hr (or 16 hr with 0.1 mol % catalyst). The solvent was then evaporated, and the product was purified using silica gel.

5-{[1,3-Benzodioxol-5-yl(methyl)amino]methyl}furan-2 (5H)-one (sample procedure). The general procedure for the oxidative Mannich reaction catalyzed by Rh2(cap)4 was followed using N,N-dimethyl-3,4-methylenedioxyaniline. Purified chromatography on silica gel (5:1→1:1 hexanes/EtOAc); orange oil: TLC R$_f$=0.36 (1:1 hexanes/EtOAc); $^1$H NMR (400 MHz, CDCl$_3$) δ 7.47 (dd, J=5.6, 1.6 Hz, 1H), 6.72 (d, J=8.3 Hz, 1H), 6.38 (d, J=2.6 Hz, 1H), 6.17-6.13 (comp, 2H), 5.89 (s, 2H), 5.24 (tt, J=5.8 Hz, 1.6 Hz, 1H), 3.64-3.53 (comp, 2H), 2.95 (s, 3H); $^{13}$C NMR (100 MHz) δ 172.6, 154.4, 148.6, 144.6, 139.8, 122.1, 108.5, 105.1, 100.8, 96.2, 81.9, 56.3, 40.3; IR (neat) 1751 (C=O) cm$^{-1}$; HRMS (EI) calcd for C$_{13}$H$_{14}$NO$_4$ 248.0923, found 248.0927 (M+H).

Example 9

Mannich Reactions

Figure 4:
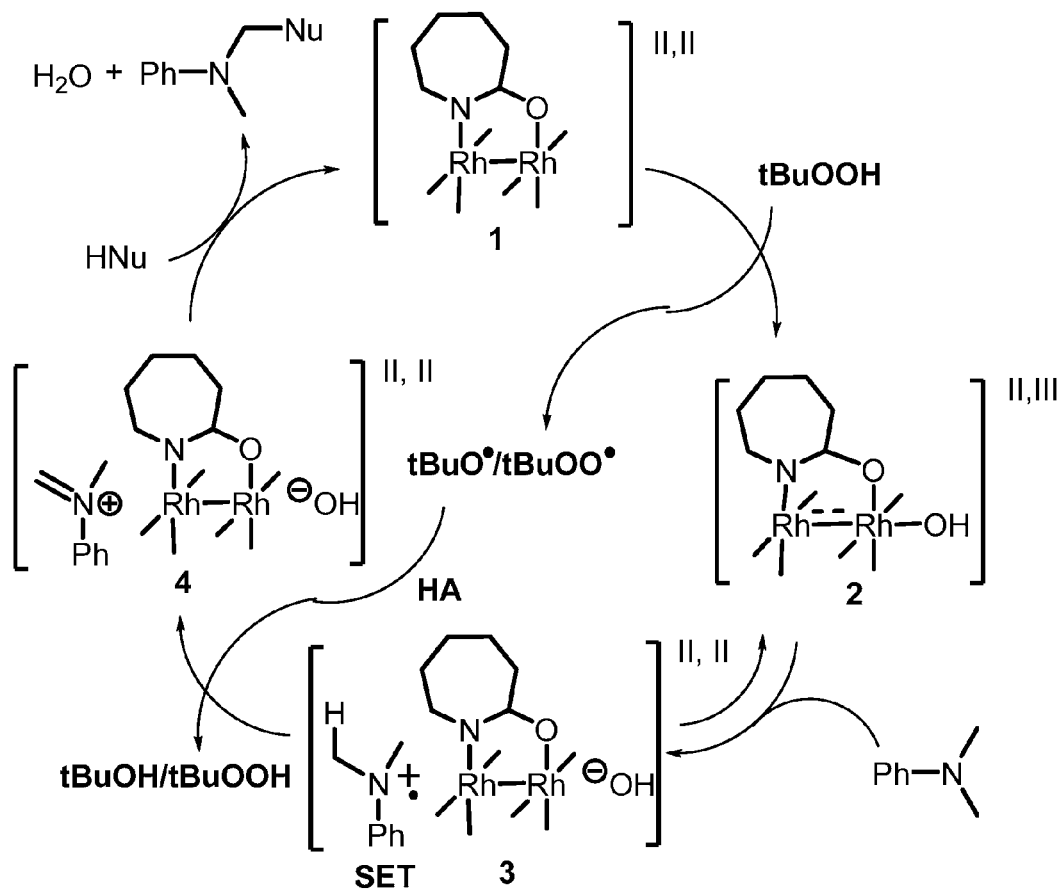
FIG. 4 illustrates the reaction pathway for Mannich Reactions conducted using the aqueous catalysis of the present invention.

The mild conditions of the optimized aqueous Rh$_2$(cap)$_4$/tert-Butyl hydroperoxide oxidation reaction of the present invention also provide a means for conducting oxodative (Table 12) and oxidative (Table 13) Mannich reactions, as shown below. The proposed catalytic cycle is shown in FIG. 4.

TABLE 12

Oxodative Mannich Reactions

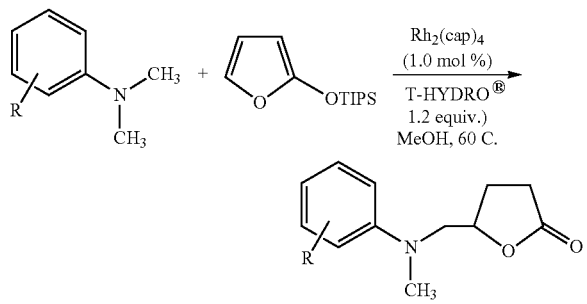

Oxodative Mannich Reaction

| Entry | Tertiary Amine Substrate | Product | % Yield |
|---|---|---|---|
| 1 | 4-tert-butyl-N,N-dimethylaniline | 5-{[(4-tert-butylphenyl)(methyl)amino]methyl}furan-2(5H)-one | 89 |
| 2 | 2-vinyl-N,N-dimethylaniline | 5-{[(2-vinylphenyl)(methyl)amino]methyl}furan-2(5H)-one | 60 |

TABLE 12-continued

| # | Substrate | Product | Yield |
|---|---|---|---|
| 3 | 4-(dimethylamino)benzaldehyde | 4-[N-methyl-N-(5-oxo-2,5-dihydrofuran-2-ylmethyl)amino]benzaldehyde | 50 |
| 4 | 1-phenylpyrrolidine | 5-(1-phenylpyrrolidin-2-yl)furan-2(5H)-one (1:1) | 89 |
| 5 | N-ethyl-N-methylaniline | 5-[(N-ethyl-N-phenylamino)methyl]furan-2(5H)-one | 64 |
| 6 | N,N,4-trimethylaniline | 5-{[N-methyl-N-(4-methylphenyl)amino]methyl}furan-2(5H)-one | 74 |
| 7 | 4-bromo-N,N-dimethylaniline | 5-{[N-(4-bromophenyl)-N-methylamino]methyl}furan-2(5H)-one | 78 |
| 8 | N-methyl-N-(3-phenylpropyl)aniline | 5-{[N-phenyl-N-(3-phenylpropyl)amino]methyl}furan-2(5H)-one | 53 |
| 10 | 2-phenyl-1,2,3,4-tetrahydroisoquinoline | 5-(2-phenyl-1,2,3,4-tetrahydroisoquinolin-1-yl)furan-2(5H)-one | 79 |

TABLE 13

Oxidative Mannich Reactions

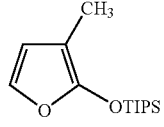

Oxidative Mannich Reaction

| Entry | Triisopropoxysilylfuran Derivative | Product | % Yield |
|---|---|---|---|
| 1 | 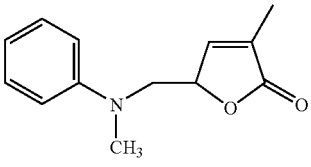 | | 86 |
| 2 | 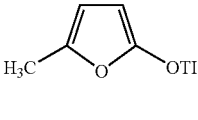 | | 72 |
| 3 | 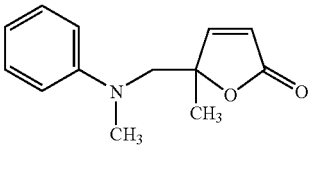 | | 75 |

The results suggest that the reactions proceed via an iminium ion intermediate, such that in a non-nucleophilic solvent:

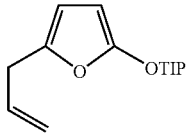

and in a nucleophilic solvent:

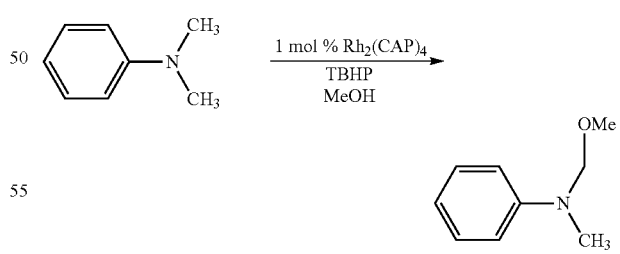

The reaction thus is analogous to the demethylation of substituted dimethylanilines mediated by Cytochrome P450.

Example 10

Oxidation of Phenols

The mild conditions of the optimized aqueous $Rh_2(cap)_4$/tert-Butyl hydroperoxide oxidation reaction of the present invention also provide a means for oxidizing phenols. Phenol was reacted with 0.1 mol % Rh$_2$(cap)$_4$, 3 equiv. of T-HYDRO®, 0.5 equiv. of NaHCO$_3$, and dichloromethane as co-solvent (Table 14).

TABLE 14

| Entry | Phenol Substrate | Product | % Yield |
|---|---|---|---|
| 1 | HO–C$_6$H$_4$–CH$_3$ | O=C$_6$H$_4$(CH$_3$)(OO$^t$Bu) | 83 |
| 2 | HO–C$_6$H$_4$–$^i$Pr | O=C$_6$H$_4$($^i$Pr)(OO$^t$Bu) | 67 |
| 3 | HO–C$_6$H$_4$–Bn | O=C$_6$H$_4$(Bn)(OO$^t$Bu) | 62 |
| 4 | HO–C$_6$H$_4$–CH$_2$COOMe | O=C$_6$H$_4$(CH$_2$COOMe)(OO$^t$Bu) | 44 |
| 5 | HO–C$_6$H$_3$(Me)–Me | O=C$_6$H$_3$(Me)(Me)(OO$^t$Bu) | 92 |
| 6 | 2,6-(Me$_3$C)$_2$-4-Me-phenol | 2,6-(Me$_3$C)$_2$-4-Me-4-(OO$^t$Bu)-cyclohexadienone | 95 |
| 7 | 2-(Me$_3$C)-4-(CMe$_3$)-phenol | 2-(Me$_3$C)-4-(CMe$_3$)-4-(OO$^t$Bu)-cyclohexadienone | 93 |

Example 11

Aziridination

Rh$_2$(cap)$_4$ is an effective catalyst of aziridination (United States Patent Publication No. 20060211870; Catino, A. J. et al. (2005) Organic Lett. 7:2787). The reaction may be depicted as follows:

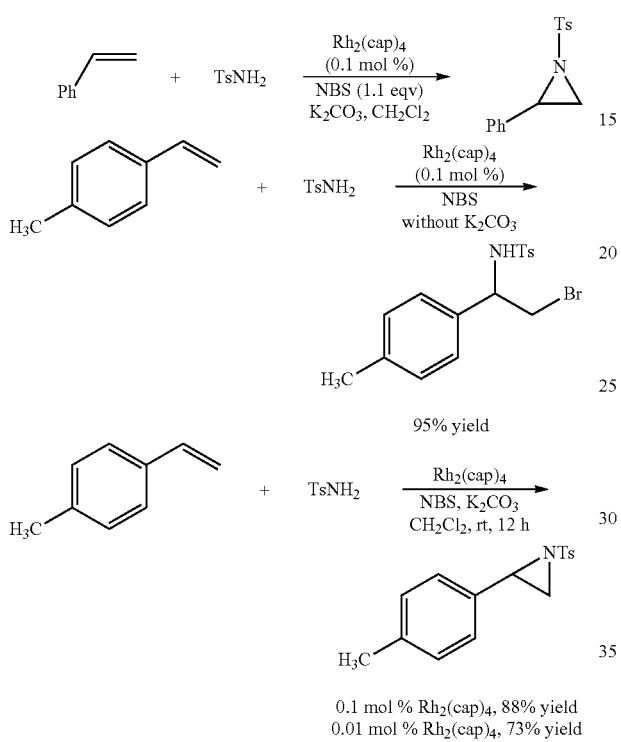

Examples of representative substrates for aziridination are shown in Table 15.

TABLE 15

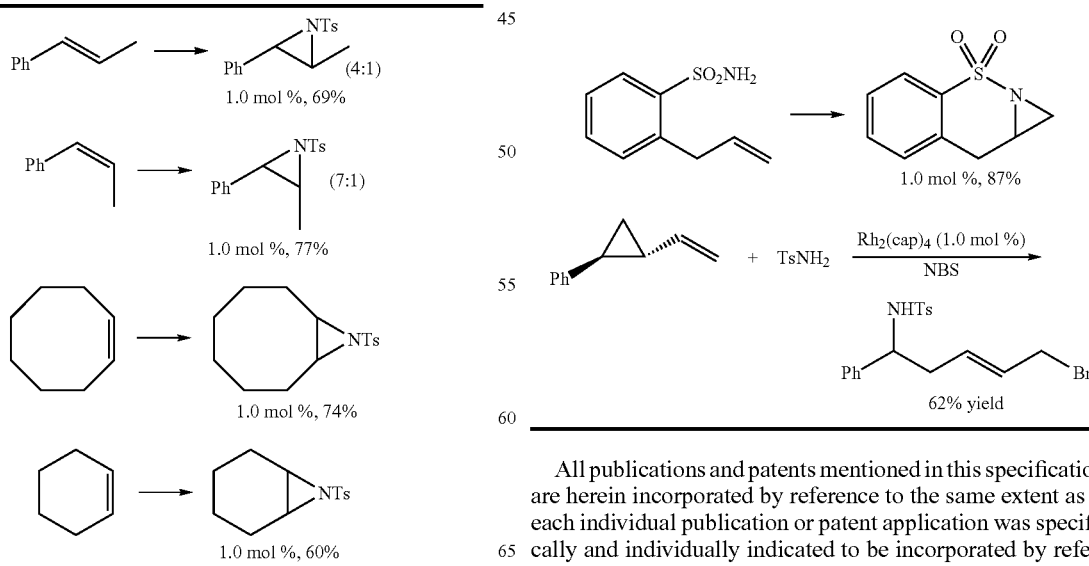

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for conducting oxidation of an allylic group of a compound, which comprises incubating a compound having an allylic group in the presence of:
    (A) a mixed-valent dirhodium(II,III) catalyst ($Rh_2^{5+}$); and
    (B) an aqueous solution of tert-butyl hydroperoxide
    under conditions sufficient to oxidize said allylic group of said compound.

2. The method of claim 1, wherein said mixed-valent dirhodium(II,III) catalyst ($Rh_2^{5+}$) is a member of the carboxamidate class of dirhodium(II,II) paddlewheel complexes.

3. The method of claim 2, wherein the arms of said carboxamidate class of dirhodium(II,II) paddlewheel complexes comprises seven membered rings.

4. The method of claim 3, wherein said mixed-valent dirhodium(II,III) catalyst ($Rh_2^{5+}$) is dirhodium(II,II) caprolactamate $[Rh_2(cap)_4]$.

5. The method of claim 1, wherein said compound is dissolved in an organic solvent.

6. The method of claim 1, wherein said organic solvent is dichloroethane or dichloromethane.

7. The method of claim 1, wherein said mixed-valent dirhodium(II,III) catalyst ($Rh_2^{5+}$) is present in said incubation at 0.4-0.6 molar equivalents.

8. The method of claim 1, wherein said tert-butyl hydroperoxide is present in said incubation at 9 or fewer molar equivalents.

9. The method of claim 1, wherein said compound has a $C_5$-$C_{12}$ alkenyl moiety which is optionally substituted with N, S, O or halogen, and that has said allylic group.

10. The method of claim 1, wherein said compound has the structure:

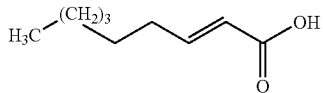

and said method results in the production of a compound having the structure:

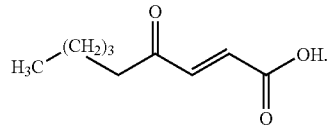

11. The method of claim 1, wherein said compound has a cyclohexene moiety which is optionally substituted with N, S, O or halogen, and that has said allylic group or is bonded to a carbon having an allylic methylene group.

12. The method of claim 1, wherein said compound has an aromatic moiety which is optionally substituted with N, S, O or halogen, and that has said allylic group or is bonded to a carbon having an allylic methylene group.

13. The method of claim 1, wherein said compound has a steroidal moiety which is optionally substituted with N, S, O or halogen, and that has said allylic group, wherein said steroidal moiety has the structure:

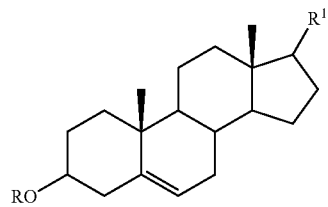

wherein R is H or a $C_2$-$C_8$ alkyl or alkenyl group which is optionally substituted with N, S, O or halogen, and R1 is O or a $C_2$-$C_8$ alkyl or alkenyl group which is optionally substituted with N, S, O or halogen.

14. The method of claim 1, wherein said compound has an enone moiety that has said allylic group.

15. The method of claim 1, wherein said compound has an enamide moiety that has said allylic group.

16. The method of claim 1, wherein said compound has an enol ether moiety that has said allylic group.

\* \* \* \* \*